US011833116B2

(12) United States Patent
Lin et al.

(10) Patent No.: US 11,833,116 B2
(45) Date of Patent: Dec. 5, 2023

(54) PREPARATION METHOD OF YEAST POWDER RICH IN NICOTINAMIDE MONONUCLEOTIDE, YEAST POWDER, AND METHODS FOR IMPROVING SKIN CONDITION, HAIR HEALTH, ANTIINFLAMMATION, CARDIOVASCULAR HEALTH, ANTIOXIDATION, ANTIAGING AND/OR RELIEVING BODY FATIGUE

(71) Applicant: TCI CO., LTD., Taipei (TW)

(72) Inventors: Yung-Hsiang Lin, Taipei (TW); Pei-Yi Wu, Taipei (TW)

(73) Assignee: TCI CO., LTD., Taipei (TW)

( * ) Notice: Subject to any disclaimer, the term of this patent is extended or adjusted under 35 U.S.C. 154(b) by 309 days.

(21) Appl. No.: 17/411,067

(22) Filed: Aug. 25, 2021

(65) Prior Publication Data

US 2022/0062158 A1 Mar. 3, 2022

Related U.S. Application Data

(60) Provisional application No. 63/069,729, filed on Aug. 25, 2020.

(51) Int. Cl.

| | | |
|---|---|---|
| *A61K 8/9728* | (2017.01) | |
| *A61K 8/67* | (2006.01) | |
| *A61K 8/49* | (2006.01) | |
| *A61K 8/64* | (2006.01) | |
| *A61Q 19/00* | (2006.01) | |
| *A61P 39/06* | (2006.01) | |
| *A61Q 19/08* | (2006.01) | |
| *A61K 36/06* | (2006.01) | |
| *A61K 31/455* | (2006.01) | |
| *A61K 31/405* | (2006.01) | |
| *A61K 38/08* | (2019.01) | |
| *A61Q 5/00* | (2006.01) | |

(52) U.S. Cl.
CPC ............ *A61K 8/9728* (2017.08); *A61K 8/492* (2013.01); *A61K 8/64* (2013.01); *A61K 8/675* (2013.01); *A61K 31/405* (2013.01); *A61K 31/455* (2013.01); *A61K 36/06* (2013.01); *A61K 38/08* (2013.01); *A61P 39/06* (2018.01); *A61Q 5/00* (2013.01); *A61Q 19/00* (2013.01); *A61Q 19/08* (2013.01)

(58) Field of Classification Search
CPC .................................................. A61K 36/064
See application file for complete search history.

(56) References Cited

U.S. PATENT DOCUMENTS

| 3,650,898 A | 3/1972 | Nakayama et al. |
|---|---|---|
| 2016/0287621 A1 | 10/2016 | Sinclair et al. |

FOREIGN PATENT DOCUMENTS

| CN | 111093397 A | | 5/2020 |
|---|---|---|---|
| CN | 111225657 A | | 6/2020 |
| WO | WO 95/01422 | * | 1/1995 |
| WO | 2015069860 A1 | | 5/2015 |
| WO | 2017022768 A1 | | 2/2017 |
| WO | 2017200050 A1 | | 11/2017 |
| WO | 2020097116 A1 | | 5/2020 |

OTHER PUBLICATIONS

Paalme et al., World J Microbiol Biotechnol, 2014; 30: 2351-2359 (Year: 2014).*
The Production of Coenzyme Q10 in Microorganisms, Corinne P. Cluis et al., Reprogramming Microbial Metabolic Pathways, 2012, Chapter 15, p. 303-310.

* cited by examiner

*Primary Examiner* — Brian Gangle
*Assistant Examiner* — Lakia J Jackson-Tongue
(74) *Attorney, Agent, or Firm* — Chieh-Mei Wang

(57) ABSTRACT

The present invention discloses yeast powder rich in nicotinamide mononucleotide, a preparation method and uses thereof. The preparation method includes: preparing a first medium, a second medium, and a third medium; inoculating the first medium with yeast for fermentation to obtain a first fermentation broth; inoculating the second medium with the first fermentation broth for fermentation to obtain a second fermentation broth; inoculating the third medium with the second fermentation broth for fermentation to obtain a third fermentation broth; centrifuging the third fermentation broth to obtain a fermented product; and drying the fermented product to obtain the yeast powder. Components of the first medium, the second medium and the third medium include nicotinamide, tryptophan and niacin. The content of nicotinamide mononucleotide in the yeast powder is at least 5000 ppm.

6 Claims, 10 Drawing Sheets

Specification includes a Sequence Listing.

SEQUENCE LISTING

<160> NUMBER OF SEQ ID NOS: 27

<210> SEQ ID NO 1
<211> LENGTH: 22
<212> TYPE: DNA
<213> ORGANISM: Artificial Sequence
<220> FEATURE:

```
<223> OTHER INFORMATION: PARP2-F

<400> SEQUENCE: 1
agcaagatga atctgtgaag gc                                              22

<210> SEQ ID NO 2
<211> LENGTH: 20
<212> TYPE: DNA
<213> ORGANISM: Artificial Sequence
<220> FEATURE:
<223> OTHER INFORMATION: PARP2-R

<400> SEQUENCE: 2
cactgaagtt cctctgggca                                                 20

<210> SEQ ID NO 3
<211> LENGTH: 19
<212> TYPE: DNA
<213> ORGANISM: Artificial Sequence
<220> FEATURE:
<223> OTHER INFORMATION: CCT5-F

<400> SEQUENCE: 3
ataaatgtga ggctgaatc                                                  19

<210> SEQ ID NO 4
<211> LENGTH: 18
<212> TYPE: DNA
<213> ORGANISM: Artificial Sequence
<220> FEATURE:
<223> OTHER INFORMATION: CCT5-R

<400> SEQUENCE: 4
acttgtcact tgtggcac                                                   18

<210> SEQ ID NO 5
<211> LENGTH: 21
<212> TYPE: DNA
<213> ORGANISM: Artificial Sequence
<220> FEATURE:
<223> OTHER INFORMATION: CCT6A-F

<400> SEQUENCE: 5
tgtgtatctt aatccagact c                                               21

<210> SEQ ID NO 6
<211> LENGTH: 20
<212> TYPE: DNA
<213> ORGANISM: Artificial Sequence
<220> FEATURE:
<223> OTHER INFORMATION: CCT6A-R

<400> SEQUENCE: 6
cgtttcacct aagagttgtc                                                 20

<210> SEQ ID NO 7
<211> LENGTH: 24
<212> TYPE: DNA
<213> ORGANISM: Artificial Sequence
<220> FEATURE:
<223> OTHER INFORMATION: CCT7-F

<400> SEQUENCE: 7
gtggcatgga caagcttatt gtag                                            24
```

-continued

```
<210> SEQ ID NO 8
<211> LENGTH: 19
<212> TYPE: DNA
<213> ORGANISM: Artificial Sequence
<220> FEATURE:
<223> OTHER INFORMATION: CCT7-R

<400> SEQUENCE: 8
cagaattgtg gccccatca                                                  19

<210> SEQ ID NO 9
<211> LENGTH: 17
<212> TYPE: DNA
<213> ORGANISM: Artificial Sequence
<220> FEATURE:
<223> OTHER INFORMATION: CCT8-F

<400> SEQUENCE: 9
acccggaggt ggagcaa                                                    17

<210> SEQ ID NO 10
<211> LENGTH: 25
<212> TYPE: DNA
<213> ORGANISM: Artificial Sequence
<220> FEATURE:
<223> OTHER INFORMATION: CCT8-R

<400> SEQUENCE: 10
ggacatgtct ctccatatga tgtga                                           25

<210> SEQ ID NO 11
<211> LENGTH: 20
<212> TYPE: DNA
<213> ORGANISM: Artificial Sequence
<220> FEATURE:
<223> OTHER INFORMATION: Parkin-F

<400> SEQUENCE: 11
gcagagaccg tggagaaaag                                                 20

<210> SEQ ID NO 12
<211> LENGTH: 20
<212> TYPE: DNA
<213> ORGANISM: Artificial Sequence
<220> FEATURE:
<223> OTHER INFORMATION: Parkin-R

<400> SEQUENCE: 12
cttttctcca cggtctctgc                                                 20

<210> SEQ ID NO 13
<211> LENGTH: 23
<212> TYPE: DNA
<213> ORGANISM: Artificial Sequence
<220> FEATURE:
<223> OTHER INFORMATION: Atg1-F

<400> SEQUENCE: 13
caggaggacg agaacacggt gtc                                             23

<210> SEQ ID NO 14
<211> LENGTH: 23
<212> TYPE: DNA
<213> ORGANISM: Artificial Sequence
<220> FEATURE:
<223> OTHER INFORMATION: Atg1-R
```

```
<400> SEQUENCE: 14
ggaaggttct tggcaccag cac                                             23

<210> SEQ ID NO 15
<211> LENGTH: 20
<212> TYPE: DNA
<213> ORGANISM: Artificial Sequence
<220> FEATURE:
<223> OTHER INFORMATION: Atg8-F

<400> SEQUENCE: 15
ccgcagtagg tggcaaagta                                                20

<210> SEQ ID NO 16
<211> LENGTH: 20
<212> TYPE: DNA
<213> ORGANISM: Artificial Sequence
<220> FEATURE:
<223> OTHER INFORMATION: Atg8-R

<400> SEQUENCE: 16
ggagtcggag aggattgctg                                                20

<210> SEQ ID NO 17
<211> LENGTH: 19
<212> TYPE: DNA
<213> ORGANISM: Artificial Sequence
<220> FEATURE:
<223> OTHER INFORMATION: FOXO-F

<400> SEQUENCE: 17
cggacaaacg gctcactct                                                 19

<210> SEQ ID NO 18
<211> LENGTH: 21
<212> TYPE: DNA
<213> ORGANISM: Artificial Sequence
<220> FEATURE:
<223> OTHER INFORMATION: FOXO-R

<400> SEQUENCE: 18
ggacccgcat gaatcgacta t                                              21

<210> SEQ ID NO 19
<211> LENGTH: 21
<212> TYPE: DNA
<213> ORGANISM: Artificial Sequence
<220> FEATURE:
<223> OTHER INFORMATION: SIRT1-F

<400> SEQUENCE: 19
tgctggccta atagagtggc a                                              21

<210> SEQ ID NO 20
<211> LENGTH: 20
<212> TYPE: DNA
<213> ORGANISM: Artificial Sequence
<220> FEATURE:
<223> OTHER INFORMATION: SIRT1-R

<400> SEQUENCE: 20
ctcagcgcca tggaaaatgt                                                20

<210> SEQ ID NO 21
<211> LENGTH: 20
```

<212> TYPE: DNA
<213> ORGANISM: Artificial Sequence
<220> FEATURE:
<223> OTHER INFORMATION: NADSYN-F

<400> SEQUENCE: 21
gcaaaatgtg caggctcgaa                    20

<210> SEQ ID NO 22
<211> LENGTH: 20
<212> TYPE: DNA
<213> ORGANISM: Artificial Sequence
<220> FEATURE:
<223> OTHER INFORMATION: NADSYN-R

<400> SEQUENCE: 22
gcactggagc agtcgtactt                    20

<210> SEQ ID NO 23
<211> LENGTH: 18
<212> TYPE: DNA
<213> ORGANISM: Artificial Sequence
<220> FEATURE:
<223> OTHER INFORMATION: MRPS5-F

<400> SEQUENCE: 23
gtccggacag tccctcac                      18

<210> SEQ ID NO 24
<211> LENGTH: 21
<212> TYPE: DNA
<213> ORGANISM: Artificial Sequence
<220> FEATURE:
<223> OTHER INFORMATION: MRPS5-R

<400> SEQUENCE: 24
cccaataaat gacctgccgt c                  21

<210> SEQ ID NO 25
<211> LENGTH: 18
<212> TYPE: DNA
<213> ORGANISM: Artificial Sequence
<220> FEATURE:
<223> OTHER INFORMATION: SOD3-F

<400> SEQUENCE: 25
agctggaaag gtgcccga                      18

<210> SEQ ID NO 26
<211> LENGTH: 21
<212> TYPE: DNA
<213> ORGANISM: Artificial Sequence
<220> FEATURE:
<223> OTHER INFORMATION: SOD3-R

<400> SEQUENCE: 26
cttggcgtac atgtctcgga t                  21

<210> SEQ ID NO 27
<211> LENGTH: 9

```
<212> TYPE: PRT
<213> ORGANISM: Saccharomyces cerevisiae TCI907

<400> SEQUENCE: 27

Met Val Ala Lys Ala His Ser Lys Lys
1               5
```

PREPARATION METHOD OF YEAST POWDER RICH IN NICOTINAMIDE MONONUCLEOTIDE, YEAST POWDER, AND METHODS FOR IMPROVING SKIN CONDITION, HAIR HEALTH, ANTIINFLAMMATION, CARDIOVASCULAR HEALTH, ANTIOXIDATION, ANTIAGING AND/OR RELIEVING BODY FATIGUE

CROSS-REFERENCE TO RELATED APPLICATION

This application claims the benefit of U.S. provisional application Ser. No. 63/069,729, filed on Aug. 25, 2020. The entirety of the above-mentioned patent application is hereby incorporated by reference herein and made a part of the specification.

REFERENCE OF AN ELECTRONIC SEQUENCE LISTING

The contents of the electronic sequence listing (P201062USI_ST25.txt; Size: 5.2 KB; and Date of Creation: Aug. 25, 2021) is herein incorporated by reference in its entirety.

BACKGROUND

Technical Field

The present invention relates to yeast powder, and in particular to a preparation method of yeast powder and the yeast powder prepared by the method, wherein the yeast powder is rich in nicotinamide mononucleotide and has multiple uses.

Related Art

Studies have found that nicotinamide adenine dinucleotide ($NAD^+$) is related to the fight against cell senescence. The main physiological functions of NAD include generating 95% or more of life activity energy, repairing damaged DNA, promoting longevity proteins, etc., and $NAD^+$ is also a component of maintaining mitochondrial activity in the body.

However, $NAD^+$ cannot be obtained directly from the diet, and as humans age, the amount of $NAD^+$ naturally produced in the body decreases. Therefore, to supplement and maintain the $NAD^+$ content in the body, studies have found that $NAD^+$ precursors can be ingested to increase the $NAD^+$ content in the body.

For example, by ingesting nicotinamide mononucleotide (NMN), NMN can be converted into $NAD^+$ through the blood in the body and accelerate elimination of ageing substances accumulated in the body.

SUMMARY

Since natural nicotinamide mononucleotide contained in plants (such as cauliflower and avocado) is extremely low and difficult to extract, most of nicotinamide mononucleotide on the market today is chemically synthesized formulas. However, the process of chemical synthesis of nicotinamide mononucleotide is accompanied by some by-products. The by-products exist in nicotinamide mononucleotide products, and when such nicotinamide mononucleotide products are ingested by humans, the by-products can easily cause metabolic burden on the human liver.

In view of this, the present invention provides a preparation method of yeast powder rich in nicotinamide mononucleotide and the yeast powder prepared by the method, and further provides uses of the yeast powder prepared by the method for improving skin condition, hair health, antiinflammation, cardiovascular health, antioxidation, antiaging, and/or relieving body fatigue.

In some embodiments, the preparation method of the yeast powder rich in nicotinamide mononucleotide includes: preparing a first medium, a second medium and a third medium; inoculating the first medium with yeast for fermentation to obtain a first fermentation broth; inoculating the second medium with the first fermentation broth for fermentation to obtain a second fermentation broth; inoculating the third medium with the second fermentation broth for fermentation to obtain a third fermentation broth; centrifuging the third fermentation broth to obtain a fermented product; and drying the fermented product to obtain the yeast powder. Components of the first medium, the second medium and the third medium include nicotinamide (NAM), tryptophan and niacin. The content of nicotinamide mononucleotide (NMN) in the yeast powder is at least 5000 ppm.

In some embodiments, the first medium is inoculated with the yeast at an inoculum amount of 5 vol %, the second medium is inoculated with the first fermentation broth at an inoculum amount of 6 vol %, and the third medium is inoculated with the second fermentation broth at an inoculum amount of 10 vol %.

In some embodiments, a concentration of the nicotinamide is 0.01 wt % to 0.3 wt %, a concentration of the tryptophan is 0.1 wt/o to 0.5 w1%, and a concentration of the niacin is 0.01 wt % to 0.06 wt %.

In some embodiments, a concentration of the nicotinamide is 0.1 wt %, a concentration of the tryptophan is 0.2 wt %, and a concentration of the niacin is 0.0369 wt %.

In some embodiments, a volume ratio of the first medium to the second medium to the third medium is 3:50:500.

In some embodiments, components of the first medium, the second medium and the third medium further include any one of a *Musa* spp. peel extract, an *Aronia melanocarpa* extract, and a *Solanum lycopersicum* extract.

In some embodiments, yeast powder is prepared by the preparation method according to claim 1, and the content of nicotinamide mononucleotide (NMN) in the yeast powder is at least 5000 ppm.

In some embodiments, yeast powder is used for preparing a composition for improving skin condition, hair health, antiinflammation, cardiovascular health, antioxidation, antiaging and/or relieving body fatigue, wherein the yeast powder is prepared by the method according to claim 1, and a content of nicotinamide mononucleotide (NMN) in the yeast powder is at least 5000 ppm.

In some embodiments, improving the skin condition is to enhance skin firmness, reduce wrinkles, reduce skin roughness, or a combination thereof.

In some embodiments, the hair health is to reduce hair loss or reduce the degree of hair scantiness.

In some embodiments, the yeast powder further includes ubiquinone biosynthesis protein (COQ protein).

In some embodiments, the yeast powder is used to regulate blood fat.

In some embodiments, the yeast powder is used to reduce an expression level of C-reactive protein (CRP) of a subject.

In some embodiments, the yeast powder achieves antiaging by regulating an expression level of antiaging-related genes, activating mitochondria or reducing a brain age.

In some embodiments, the antiaging-related genes comprise CCT genes, PARP2 gene, Parkin gene, Atg genes, FOXO gene, SIRT1 gene, NADSYN gene, MRPS5 gene, SOD3 gene or a combination thereof.

In some embodiments, the yeast powder achieves the antioxidation function by reducing the damage of reactive oxygen species (ROS).

In some embodiments, a daily dose of the yeast powder is 100 mg.

In summary, according to the preparation method of yeast powder rich in nicotinamide mononucleotide of any embodiment, the yeast powder rich in nicotinamide mononucleotide can be prepared, and the content of nicotinamide mononucleotide in the yeast powder is at least 5000 ppm. The preparation method solves the problem that traditional nicotinamide mononucleotide can only be chemically synthesized and harmful by-products are generated, and at the same time solves the technical bottleneck that traditional nicotinamide mononucleotide is inedible and can only be externally used. In addition, the yeast powder prepared by the preparation method of the yeast powder rich in nicotinamide mononucleotide of any embodiment has the functions of improving skin condition (for example, enhancing skin firmness, reducing wrinkles, and reducing skin roughness), hair health (for example, reducing hair loss or reducing the degree of hair scantiness), antiinflammation, cardiovascular health, antioxidation, antiaging and/or relieving body fatigue, and can be used for preparing a composition with the above functions. In some embodiments, the yeast powder further includes ubiquinone biosynthesis protein (COQ protein). In some embodiments, the yeast powder has one or any combination of functions of regulating blood fat; reducing the expression level of C-reactive protein (CRP) of a subject; achieving antiaging by regulating the expression level of antiaging-related genes (for example, CCT genes, PARP2 gene, Parkin gene, Atg genes, FOXO gene, SIRT1 gene, NADSYN gene, MRPS5 gene, SOD3 gene or a combination thereof), activating mitochondria or reducing the brain age; and achieving antioxidation by reducing the damage of reactive oxygen species (ROS).

The following describes the present invention in detail with reference to the accompanying drawings and specific embodiments, but should not be used as a limitation on the present invention.

DETAILED DESCRIPTION

In the description of the following embodiments, unless otherwise specified, the symbol "%" refers to percentage by weight and the symbol "vol %" usually refers to concentration expressed in percentage by volume. In addition, the serial number terms "first", "second", "third", etc., described below, are used to distinguish the referred components, rather than to sort or limit the difference of the referred components, or intend to limit the scope of the present invention.

Figure 1:
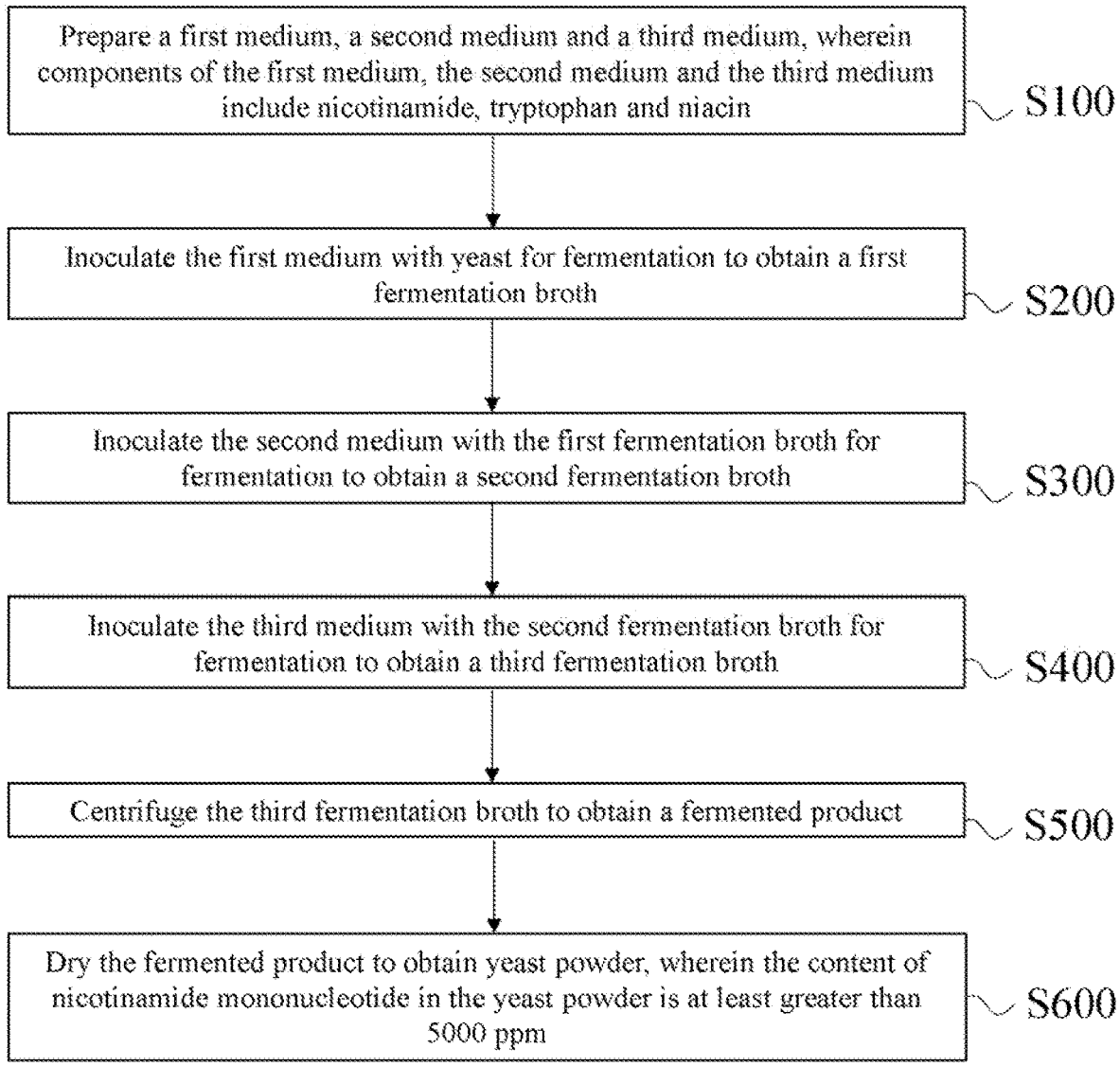
FIG. 1 is a flow chart of preparation of yeast powder rich in nicotinamide mononucleotide.

Please refer to FIG. 1. First, a first medium, a second medium and a third medium are prepared (step S100). Herein, the components of the first medium, the second medium and the third medium are the same, and include a basic medium, nicotinamide (NAM), tryptophan, niacin, etc. For example, the first medium, the second medium and the third medium are fermentation media for fermentation, and include the following components: a basic medium containing yeast peptone, yeast extract, potassium dihydrogen phosphate ($KH_2PO_4$), potassium hydrogen phosphate ($K_2HPO_4$), magnesium sulphate-7hydrate ($MgSO_4 \cdot 7H_2O$), glucose, citric acid, sodium acetate, manganese gluconate, cysteine, deionized distilled water ($ddH_2O$) and an antifoaming agent, as well as nicotinamide, tryptophan, niacin, etc. In some embodiments, glucose is one of the components of the basic medium, and is sterilized separately from other components before the fermentation medium is inoculated with a strain, and mixed with other components before the inoculation of the strain to form a sterilized fermentation medium.

In some embodiments, the components of the first medium, the second medium and the third medium include 0.01% to 0.3% of nicotinamide, 0.1% to 0.5% of tryptophan and 0.001% to 0.06% of niacin in addition to the basic medium. Preferably, the components of the first medium, the second medium and the third medium include 0.1% of nicotinamide, 0.2% of tryptophan and 0.0369% of niacin in addition to the basic medium. Based on this, when the fermentation medium contains the nicotinamide, the tryptophan and the niacin as precursors for the synthesis of nicotinamide mononucleotide, the synthesis of the nicotinamide mononucleotide by yeast is benefited.

In some embodiments, the components of the first medium, the second medium and the third medium further include a *Musa* plant extract, an *Aronia* plant extract, a *Solanum* plant extract, or any combination thereof. Herein, the *Musa* plant extract may be a *Musa* sp. peel extract, the *Aronia* plant extract may be an *Aronia melanocarpa* extract, and the *Solanum* plant extract may be a *Solanum lycopersicum* extract. For example, when the components of the fermentation medium include the basal medium, nicotinamide, tryptophan and niacin, the addition of 0.05% of *Musa* spp. peel extract, 0.085% of *Aronia melanocarpa* extract or 0.05% of *Solanum ycopersicum* extract is beneficial to increase of the content of nicotinamide mononucleotide in a fermentation broth.

In some embodiments, the *Musa* spp. peel extract may be prepared by separating the peel from pulp of *Musa* spp., and performing the following operations on the *Musa* spp. peel to provide the *Musa* spp. peel extract: 1) mixing the *Musa* spp. peel with an extraction solvent (a volume ratio of the *Musa* spp. peel to the extraction solvent is 1:6; the extraction solvent is provided according to a volume ratio of citric acid:water 1:100), and performing extraction at 85° C. for 0.5 hours to provide a crude extract; 2) centrifuging the crude extract of step 1 at 5000 rpm. for 10 minutes, and taking and filtering a supernatant with a 400-mesh filter screen to provide a filtrate; 3) at 55+/−5° C., concentrating the filtrate of step 2 under reduced pressure to provide a concentrated extract; and 4) freeze-drying the concentrated extract of step 3 to provide a dried product (i.e., the above *Musa* spp. peel extract). In some embodiments, the *Aronia melanocarpa* extract is prepared by squeezing and concentrating juice from *Aronia melanocarpa* (black chokeberry) fruits. In some embodiments, the *Solanum lycopersicum* extract is prepared by cutting *Solanum lycopersicum* (kumato) into pieces and homogenizing the pieces to form a *Solanum lycopersicum* homogenate, and then extracting the *Solanum lycopersicum* homogenate with water at 40° C. to 60° C. for 0.5 hours to 2 hours, wherein the liquid-solid ratio of the water to the *Solanum lycopersicum* homogenate is (5-20):(1-5).

In some embodiments, a volume ratio of the first medium to the second medium to the third medium is 3:50:500.

Following Step S100, the first medium is inoculated with yeast for fermentation to obtain a first fermentation broth (step S200). Herein, the yeast used may be *Saccharomyces cerevisiae*. For example, the *Saccharomyces cerevisiae* may be commercially available *Saccharomyces cerevisiae* or *Saccharomyces cerevisiae* TC1907. *Saccharomyces cerevisiae* TC1907 is a strain of *Saccharomyces cerevisiae* isolated from draft beer. *Saccharomyces cerevisiae* TC1907 is deposited at the Food Industry R&D Institute under the deposit number BCRC 920118, and at the German Collection of Microorganisms and Cell Cultures under the deposit number DSMZ33480. *Saccharomyces cerevisiae* TC1907 is aerobic yeast with an ovoid shape. The colony of *Saccharomyces cerevisiae* TC1907 is opaque and milky white, and the surface of the colony is smooth and the edges are neat. *Saccharomyces cerevisiae* TC1907 grows at a temperature of 28° C. to 37° C. In addition, *Saccharomyces cerevisiae* TC1907 may survive in an environment with a pH value of 3 to 7. In some embodiments, *Saccharomyces cerevisiae* TC1907 is resistant to gastric acid and bile salts. For example, the survival rate of *Saccharomyces cerevisiae* TC1907 in a simulated stomach environment (pH 3-4) is 99.4%, and the survival rate in a simulated intestinal environment (pH 7) is 99.8%.

In some embodiments, the first medium is inoculated with yeast at an inoculum amount of 5 vol %. For example, before inoculating with the yeast, 3 L of the first medium is prepared and sterilized at 121° C. for 30 minutes. In addition, after confirming that the components in the first medium are completely dissolved and the temperature is lowered, the first medium is inoculated with 5 vol % (equivalent to 150 mL) of yeast for subsequent fermentation. Herein, the $OD_{600}$ of the yeast for inoculation is 6 to 8.

In some embodiments, in the fermentation process of the first fermentation broth, the fermentation temperature is 30+/−1° C., the pH value is 6.5+/−0.1, and the dissolved oxygen (DO) value is maintained at 40 mg/L to 50 mg/L. In addition, the pH value of the first fermentation broth is adjusted with 10 N sodium hydroxide (NaOH).

In addition, the first fermentation broth is fermented in a fermentation tank. For example, 3 L of the first medium and 150 mL of yeast may be fermented in a 5 L fermentation tank. In some embodiments, an aeration rate set in the fermentation process of the first fermentation broth is 3 L/min, and the stirring rate is set to 250 rpm to ensure that the fermentation process is performed in an aerobic environment. In addition, before starting the fermentation, the first medium must be stirred at an aeration rate of 3 L/min and a stirring rate of 250 rpm to make the dissolved oxygen higher than 40% before inoculation.

In some embodiments, the fermentation time required for the first fermentation broth is 4 hours to 5 hours, and the $OD_{600}$ of the yeast in the first fermentation broth is 4.0 to 5.0 after the fermentation.

Following step S200, the second medium is inoculated with the first fermentation broth for fermentation to obtain a second fermentation broth (step S300).

In some embodiments, the second medium is inoculated with the first fermentation broth at an inoculum amount of 6 vol %. For example, before inoculating with the first fermentation broth, 50 L of the second medium is prepared and sterilized at 121° C. for 25 minutes to 30 minutes. In addition, after confirming that the components in the second medium are completely dissolved and the temperature is lowered, the second medium is inoculated with 6 vol % (equivalent to 3 L) of the first fermentation broth for subsequent fermentation.

In some embodiments, in the fermentation process of the second fermentation broth, the fermentation temperature is 30+/−1° C., the pH value is 6.5+/−0.1, and the dissolved oxygen (DO) value is maintained at 40 mg/L to 50 mg/L. In addition, the pH value of the second fermentation broth is adjusted with 10 N sodium hydroxide (NaOH).

In addition, the second fermentation broth is fermented in a fermentation tank. For example, 50 L of the second medium and 3 L of the first fermentation broth may be fermented in a 75 L fermentation tank. In some embodiments, an aeration rate set in the fermentation process of the second fermentation broth is 50 L/min, the stirring rate is set to 200 rpm, and the pressure value in the fermentation tank is 0.3+/−0.1 kg/cm$^2$ to ensure that the fermentation process is performed in an aerobic environment. In addition, before starting the fermentation, the second medium must be stirred at an aeration rate of 30 L/min and a stirring rate of 200 rpm to make the dissolved oxygen greater than 40% before inoculation.

In some embodiments, the fermentation time required for the second fermentation broth is 4 hours to 5 hours, and the $OD_{600}$ of the yeast in the second fermentation broth is 4.0 to 5.0 after the fermentation.

Following step S300, the third medium is inoculated with the second fermentation broth for fermentation to obtain a third fermentation broth (step S400).

In some embodiments, the third medium is inoculated with the second fermentation broth at an inoculum amount of 10 vol %. For example, before inoculating with the second fermentation broth, 500 L of the third medium is prepared and sterilized at 121° C. for 30 minutes. In addition, after confirming that the components in the third medium are completely dissolved and the temperature is lowered, the third medium is inoculated with 10 vol % (equivalent to 50 L) of the second fermentation broth for subsequent fermentation.

In some embodiments, in the fermentation process of the third fermentation broth, the fermentation temperature is 30+/−1° PC, the pH value is 6.5+/−0.1, and the dissolved oxygen (DO) value is maintained at 40 mg/L to 60 mg/L. In addition, the pH value of the third fermentation broth is adjusted with 10 N sodium hydroxide (NaOH).

In addition, the third fermentation broth is fermented in a fermentation tank. For example, 500 L of the third medium and 50 L of the second fermentation broth may be fermented in a 750 L fermentation tank. In some embodiments, the aeration rate set in the fermentation process of the third fermentation broth is 500 L/min, the stirring rate is set to 100 rpm, and the pressure value in the fermentation tank is 0.3+/−0.1 kg/cm$^2$ to ensure that the fermentation process is performed in an aerobic environment. In addition, before starting the fermentation, the third medium must be stirred at an aeration rate of 100 L/min and a stirring rate of 200 rpm to make the dissolved oxygen greater than 40%/6 before inoculation.

In some embodiments, the fermentation time required for the third fermentation broth is 12 hours to 14 hours, and the $OD_{600}$ of the yeast in the third fermentation broth is 48.0 to 53.0 after the fermentation.

Following step S400, the third fermentation broth is centrifuged to obtain a fermented product (step S500). In some embodiments, a fermented product is separated from the third fermentation broth with a centrifuge, the $OD_{600}$ of the fermented product is greater than 500, and the solid content is greater than 65% and less than 80%.

In some embodiments, the pH value during centrifugation is 6.5+/−0.1. In some embodiments, the tank pressure of a centrifuge with a capacity of 750 L is 1.0 kg/cm$^2$, and the set flow rate is 0.3 m$^3$/h.

Herein, the "fermented product" refers to a fermented product of yeast, which includes yeast cells, yeast protein (from a small amount of yeast broken in the process) and a fermentation broth (including the medium) containing metabolites of the yeast. The metabolites of the yeast refer to substances secreted by the yeast into the fermentation medium during the culture process, such as nicotinamide mononucleotide (NMN), coenzyme $Q_{10}$ and other compounds. For example, the fermented product contains nicotinamide mononucleotide (NMN), ubiquinone biosynthesis protein (COQ protein), coenzyme $Q_{10}$ and other compounds.

Following step S500, the fermented product is dried to obtain yeast powder (step S600). Herein, the obtained yeast powder contains at least $1.0 \times 10^9$ CFU/g yeast. For example, the drying method includes freeze-drying, low temperature drying, dehydration, etc.

In some embodiments, a crude fermented product is freeze-dried and pulverized to obtain the fermented product. In addition, when the freeze-drying step is performed, freeze-drying protective agents are added to protect bacterial cells in the crude fermented product from being destroyed. For example, the freeze-drying protective agents include skimmed milk powder, maltodextrin, sucrose and glycerin.

Herein, the content of nicotinamide mononucleotide (NMN) in the obtained yeast powder is at least greater than 5000 ppm, preferably 5000 ppm to 10000 ppm. For example, the content of the nicotinamide mononucleotide in the yeast powder is 5264.15 ppm.

In some embodiments, the yeast powder further includes ubiquinone biosynthesis protein (COQ protein). Ubiquinone biosynthesis protein can help yeast to synthesize $Q_{10}$ protein, so when the content of the ubiquinone biosynthesis protein is increased, the content of coenzyme $Q_{10}$ synthesized in the yeast may also be increased. Based on this, coenzyme $Q_{10}$ may also be included in the yeast powder.

In some embodiments, by the above preparation process, the content of nicotinamide mononucleotide in the yeast powder prepared by the fermentation media (that is, the first medium, the second medium and the third medium) containing nicotinamide, tryptophan, niacin and other components may be increased by at least 2 times compared with the yeast powder prepared by the fermentation media not containing nicotinamide, tryptophan and niacin.

In some embodiments, when the content of nicotinamide (NAM) in the fermentation media (that is, the first medium, the second medium and the third medium) is 0.1%, the yeast has a preferred yield of nicotinamide mononucleotide. Moreover, when the content of nicotinamide in the fermentation media is higher than 1.1%, the yield of nicotinamide mononucleotide produced by the yeast will be reduced to or lower than the yield of nicotinamide mononucleotide without nicotinamide in the media.

In some embodiments, when any one or more plant extracts of a *Solanum* plant extract (such as a *Solanum lycopersicum* extract), an *Aronia* plant extract (such as an *Aronia melanocarpa* extract), and a *Musa* plant extract (such as a *Musa* ssp. peel extract) are added to the fermentation media, the content of nicotinamide mononucleotide (NMN) in the prepared yeast powder is increased. For example, in the yeast powder prepared with a fermentation medium containing the *Musa* spp. peel extract, the content of nicotinamide mononucleotide in the yeast powder may be increased by at least 1.1 times. In some embodiments, in the yeast powder prepared with a fermentation medium containing the *Aronia melanocarpa* extract, the content of nicotinamide mononucleotide in the yeast powder may be increased by at least 1.47 times. In some embodiments, in the yeast powder prepared with a fermentation medium containing the *Solanum lycopersicum* extract, the content of nicotinamide mononucleotide in the yeast powder may be increased by at least 1.19 times.

Based on this, in the yeast powder rich in nicotinamide mononucleotide (NMN) prepared by the preparation method of any one of the embodiments, the content of nicotinamide mononucleotide is indeed increased. Besides, the following embodiments further show that the yeast powder rich in nicotinamide mononucleotide can be used for improving skin condition, hair health, antiinflammation, cardiovascular health, antioxidation, antiaging, and/or relieving body fatigue. In addition, the yeast powder rich in nicotinamide mononucleotide can be used to prepare a composition for improving skin condition, hair health, antiinflammation, cardiovascular health, antioxidation, antiaging, and/or relieving body fatigue.

In some embodiments, the yeast powder can enhance the subject's skin firmness, reduce wrinkles, reduce the subject's skin roughness, or a combination thereof, so as to improve the condition of the subject's skin. For example, after the subject takes the yeast powder, the yeast powder can reduce the subject's skin wrinkles and skin texture, and improve the subject's skin firmness, so that the subject's skin becomes smooth and elastic, and further the overall skin condition is improved. Based on this, the yeast powder has the function of improving the skin condition.

In some embodiments, the yeast powder can reduce the subject's hair loss or/and reduce the degree of the subject's hair scantiness, so as to achieve the effect of hair health. For example, after the subject takes the yeast powder, the yeast powder can reduce the subject's hair loss and change the degree of the subject's hair scantiness. Based on this, the yeast powder has the function of hair health.

In some embodiments, the yeast powder can reduce the content of reactive oxygen species (hereinafter referred to as ROS) in cells. For example, after the subject takes the yeast powder, the subject's cells can resist the cellular oxidative stress, thereby achieving an antioxidation effect.

In some embodiments, the yeast powder can increase mitochondrial activity. For example, after the subject takes the yeast powder, the mitochondrial activity of the subject's cells can be activated, thereby achieving an antioxidation and/or antiaging effect.

In some embodiments, the yeast powder can achieve antiaging by regulating the expression level of antiaging-related genes of the subject, activating mitochondria or reducing the brain age. For example, the antiaging-related genes include CCT genes, PARP2 gene (Gene ID: 10038), Parkin gene (Gene ID: 5071), Arg genes, FOXO gene (Gene ID: 2308), SIRT1 gene (Gene ID: 23411), NADSYN gene (Gene ID: 55191), MRPS5 gene (Gene ID: 64969), SOD3 gene (Gene ID: 6649) or a combination thereof. Herein, the CCT genes include CCT5 gene (Gene ID: 22948), CCT6A gene (Gene ID: 908), CCT7 gene (Gene ID: 10574), and CCT8 gene (Gene ID: 10694). The Arg genes include Arg1 gene (Gene ID: 8408) and Arg8 gene (Gene ID: 11345).

In some embodiments, when the subject takes the yeast powder, the expression levels of the CCT genes, the Parkin gene, the Atg genes, the FOXO gene, the SIRT1 gene, the NADSYN gene, the MRPS5 gene, the SOD3 gene or a combination thereof can be increased, and the expression level of the PARP2 gene can be inhibited. For example, by increasing the expression level of the CCT genes which are chaperonin capable of promoting the correction of incorrectly folded protein and sending protein that cannot be repaired successfully to proteasome for hydrolysis, cell function decline and acceleration of cell ageing and death can be avoided, and an antiaging cell regulation effect can be achieved. Increasing the expression level of the Parkin gene can promote the recovery of mature cells into young cells. Inhibiting the expression level of the PARP2 gene can promote the activity of telomerase and cell rejuvenation, and ensure that the end of DNA does not lack telomerase during replication, so as to reduce the probability of cell ageing. Increasing the expression levels of the Atg genes and the MRPS5 gene can improve the antiaging ability of cells and prolong the cell life span. Increasing the expression level of the FOXO gene can remove ageing cells to protect young cells. Increasing the expression level of the SIRT1 gene can regulate important metabolic functions of the body. Increasing the expression level of the NADSYN gene can achieve an antioxidation effect.

In some embodiments, when the subject is supplemented with nicotinamide mononucleotide after taking the yeast powder, the expression level of the downstream regulatory genes (such as the SIRT1 gene and the SOD3 gene) of nicotinamide adenine dinucleotide ($NAD^+$) in the subject's blood increases, indicating that the yeast powder can activate the mitochondria of the subject's cells and has antiaging ability.

In some embodiments, the yeast powder is used to reduce an expression level of C-reactive protein (CRP) of a subject. Due to conditions such as damage to body tissues and chronic inflammation, the amount of C-reactive protein in the blood will increase, so C-reactive protein can be used as a risk indicator for inflammation and cardiovascular diseases. For example, after the subject takes the yeast powder, the level of C-reactive protein in the blood can be reduced, indicating that the subject's risk of cardiovascular diseases is reduced. Based on this, the yeast powder has an antiinflammatory function.

In some embodiments, the yeast powder can be used to regulate blood fat. Herein, regulating blood fat refers to inhibiting the level of low-density lipoprotein cholesterol (LDL-C) and reducing the ratio of low-density lipoprotein cholesterol to high-density lipoprotein cholesterol (T.CHOL/HDL). For example, after the subject is supplemented with nicotinamide mononucleotide after taking the yeast powder, the level of low-density lipoprotein cholesterol in the blood of the subject decreases, and the ratio of low-density lipoprotein cholesterol to high-density lipoprotein cholesterol decreases, indicating that the subject's risk of suffering from coronary atherosclerosis decreases. Based on this, the yeast powder can be used to regulate blood fat and have a cardiovascular health function.

In some embodiments, the yeast powder can reduce the brain age. For example, after taking the yeast powder, the subject's brain age tested can be decreased by at least 10 years, indicating that when the brain age is tested, the subject's mind is clearer and the brain age tested is younger. Based on this, the yeast powder has an antiaging function.

In some embodiments, the yeast powder can be used to improve the physical fatigue of the subject. For example, after taking the yeast powder, the physical fatigue of the subject can be effectively reduced.

In some embodiments, the yeast powder can be re-dissolved in a lysis buffer and reacted with DNase with a concentration of 1 µg/mL for 10 minutes to decompose the DNA of the yeast powder. Then, the bacteria are broken by a high-pressure breaker three times sequentially at 25 kilopound per square inch (Kpsi), 30 Kpsi and 32 Kpsi to form a yeast extract. The yeast extract contains at least 5000 ppm of nicotinamide mononucleotide. In some embodiments, the yeast extract further includes ubiquinone biosynthesis protein (COQ protein) and coenzyme $Q_{10}$. In addition, since the raw material of the yeast extract is yeast powder, the yeast extract also has the functions of improving the skin condition, hair health, antiinflammation, cardiovascular health, antioxidation, antiaging, and/or relieving body fatigue that the yeast powder has.

Herein, the "yeast extract" refers to yeast protein and the substances contained in the raw material (yeast powder), and the substances contained in the raw material (yeast powder) may be the metabolites of the yeast and the medium.

Based on this, the yeast powder rich in nicotinamide mononucleotide prepared by the preparation method of any embodiment and/or the yeast extract prepared by the yeast powder can be used to prepare a composition for improving skin condition, hair health, antiinflammation, cardiovascular health, antioxidation, antiaging, and/or relieving body fatigue. Herein, the composition contains at least 5000 ppm of nicotinamide mononucleotide. In some embodiments, the composition further includes ubiquinone biosynthesis protein (COQ protein).

In some embodiments, the composition may be solid (such as powders, tablets, capsules, etc.). In some embodiments, a daily dose of the yeast powder is 100 mg. That is, the dose of the composition is 100 mg of yeast powder per day.

In some embodiments, any of the above composition may be pharmaceuticals. In other words, the pharmaceuticals contain an effective content of yeast powder and/or yeast extract prepared from the yeast powder.

In some embodiments, the pharmaceuticals may be manufactured in a dosage form suitable for intestinal, parenteral, oral, or topical administration using techniques well known to those skilled in the art.

In some embodiments, the dosage form for intestinal or oral administration may be, but is not limited to, tablets, troches, lozenges, pills, capsules, dispersible powders or granules, solutions, suspensions, emulsions, syrups, elixirs, slurries or the like. In some embodiments, the dosage form for parenteral or topical administration may be, but is not limited to, injections, sterile powders, external preparations, or the like. In some embodiments, the administration method of the injection can be subcutaneous injection, intraepidermal injection, intradermal injection, or intralesional injection.

In some embodiments, the above pharmaceuticals may include pharmaceutically acceptable carriers that are widely used in pharmaceutical manufacturing technology. In some embodiments, the pharmaceutically acceptable carriers may be one or more of the following carriers: solvents, buffers, emulsifiers, suspending agents, decomposers, disintegrating agents, dispersing agents, binding agents, excipients, stabilizing agents, chelating agents, diluents, gelling agents, preservatives, wetting agents, lubricants, absorption delaying agents, liposomes, and the like. The type and quantity of the selected carriers fall within the scope of professionalism and routine technology of those skilled in the art. In some embodiments, the solvents as a pharmaceutically acceptable carrier may be water, normal saline, phosphate buffered saline (PBS), or an aqueous solution containing alcohol.

In some embodiments, any of the above compositions may be edible products. In other words, the edible products contain a specific content of yeast powder and/or yeast extract prepared from the yeast powder. In some embodiments, the edible products may be general foods, health foods or dietary supplements.

In some embodiments, the above edible products may be manufactured in a dosage form suitable for oral administration by using techniques well known to those skilled in the art. In some embodiments, the general foods may be the edible products. In some embodiments, the general foods may be, but are not limited to, beverages, fermented foods, bakery products or seasonings.

In some embodiments, the obtained yeast powder and/or the yeast extract prepared from the yeast powder may be further used as a food additive to prepare a food composition containing the yeast powder and/or the yeast extract prepared from the yeast powder. Herein, the yeast powder of any embodiment may be added during the preparation of raw materials by a conventional method, or the yeast powder of any embodiment may be added in the food production process, to prepare an edible product (that is, a food composition) with any edible material for humans and non-human animals to eat.

Example 1: Fermentation Process: Preparation of Yeast Powder Rich in Nicotinamide Mononucleotide (NMN)

Fermentation media were prepared and divided into a first medium, a second medium and a third medium according to the fermentation sequence. Herein, each fermentation medium included a basic medium, nicotinamide, tryptophan and niacin, and specifically included the following components: 2.0% of yeast peptone (English trade name: Yeast peptone GLS: manufacturer: STBIO MEDIA, INC.), 2.0% of yeast extract 902 (English trade name: Angel yeast extract 902; manufacturer: De'en Biomedical Co., Ltd.), 0.5% of potassium dihydrogen phosphate (manufacturer: Sigma-Aldrich), 0.5% of potassium hydrogen phosphate (manufacturer: Zimi Chemicals Co., Ltd.), 0.05% of magnesium sulfate (manufacturer: Grand union Industrial Co., Ltd.), 10% of glucose (manufacturer: LYNNBROS Industrial Co., Ltd.), 0.17% of citric acid (manufacturer: UNION Food Co., Ltd.), 0.5% of sodium acetate (manufacturer: UNION Food Co., Ltd.), 0.016% of manganese gluconate (manufacturer: Maylong Trading Co., Ltd.), 0.1% of cysteine (manufacturer: LYNNBROS Industrial Co., Ltd.), 0.05% of an antifoaming agent (manufacturer: HEALTHCARE PLUS Co., Ltd.), 0.1% of nicotinamide (manufacturer: Sigma-Aldrich), 0.2% of tryptophan (manufacturer: Sigma-Aldrich) and 0.0369% of niacin (manufacturer. Sigma-Aldrich), which were made up to 100% with deionized distilled water. The glucose was sterilized separately from other components. Herein, the volume of the first medium was 3 L, the volume of the second medium was 50 L, and the volume of the third medium was 500 L.

3 L of the sterilized first medium was placed in a 5 L fermentation tank, wherein the dissolved oxygen of the first medium must be higher than 40% for subsequent inoculation. *Saccharomyces cerevisiae* TCI907 was first activated to make the $OD_{600}$ 6-8, then the first medium with an oxygen content of higher than 40% was inoculated with the activated *Saccharomyces cerevisiae* TC1907 at an inoculum amount of 5 vol % (that is, 150 mL) to perform first fermentation to form a first fermentation broth, and the fermentation time was 4 hours to 5 hours. In the fermentation process of the first fermentation broth, the fermentation temperature was 30+/−1° C., the pH value was 6.5+/−0.1, and the dissolved oxygen value was maintained at 40 mg/L to 50 mg/L.

After the fermentation of the first fermentation broth was completed, the $OD_{600}$ was 4.0 to 5.0. Next, a 75 L fermentation tank containing 50 L of the second medium was inoculated with the first fermentation broth at an inoculum amount of 6 vol % (that is, 3 L) to perform second fermentation to form a second fermentation broth, and the fermentation time was 4 hours to 5 hours. The dissolved oxygen of the second medium must be higher than 40%. In addition, in the fermentation process of the second fermentation broth, the fermentation temperature was 30+/−1° C., the pH value was 6.5+/−0.1, and the dissolved oxygen value was maintained in a range of 40 mg/L to 50 mg/L.

After the fermentation of the second fermentation broth was completed, the $OD_{600}$ was 4.0 to 5.0. Next, a 750 L fermentation tank containing 500 L of the third medium was inoculated with the second fermentation broth at an inoculum amount of 10 vol % (that is, 50 L) to perform third fermentation to form a third fermentation broth, and the fermentation time was 12 hours to 14 hours. The dissolved oxygen of the third medium must be higher than 40%. In addition, in the fermentation process of the third fermentation broth, the fermentation temperature was 30+/−1° C. the pH value was 6.5+/−0.1, and the dissolved oxygen value was maintained in a range of 40 mg/L to 50 mg/L.

After the fermentation of the third fermentation broth was completed, the $OD_{600}$ was 48.0 to 53.0. Then, the third fermentation broth was transferred to a centrifuge to obtain a fermented product with a solid content of higher than 65% and less than 80%, and an $OD_{600}$ of higher than 500. In addition, 40 g of skimmed milk powder, 120 g of maltodextrin, 80 g of sucrose and 40 g of glycerin used as freeze-drying protective agents were added to each kilogram of the fermented product, and the mixture was freeze-dried and pulverized to obtain yeast powder.

Example 2: Fermentation Process: Yeast Strain Test

Herein, the content of nicotinamide mononucleotide (NMN) in the yeast powder was used as a judgment index.

An experimental group was the yeast powder prepared in Example 1, and the yeast strain used was *Saccharomyces cerevisiae* TC1907.

Yeast powder of a comparison group was prepared according to the preparation process of Example 1 but the strain used in Example 1 was replaced. In other words, the difference from the preparation process of Example 1 was that the yeast strain used in the preparation process of the comparison group was *Cyberlindnera jadinii* (purchased from the Bioresource Collection and Research Center of the Food Industry R&D Institute in Taiwan, China, with the deposit number BCRC20325).

1 gram of yeast powder was taken from each of the experimental group and the comparison group and dissolved in 9 grams of water to form a yeast solution separately, and the yeast cells were disrupted with a cell disrupter (brand: Sunway Scientific Co., Ltd.) on ice. Then, the yeast solutions of the experimental group and the comparison group after the cell disruption treatment and a reaction solution were added to a 96-well plate separately, and reacted on ice for 2 minutes, and then 88% formic acid (a commercially available product) was added and reacted at 37° C. for another 10 minutes to obtain solutions to be assayed. Herein, the reaction solution included 20% acetophenone (a commercially available product) dissolved in DMSO, and 2M potassium hydroxide (a commercially available product).

Commercially available NMN (manufacturer: Wuxi Cima Science Co., Ltd.) was serially diluted into NMN samples with different concentrations in a range of 0.04 mM to 0.000625 mM, and 250 μL of each sample was added to a 96-well plate separately to facilitate subsequent production of an NMN concentration standard line.

Then, the solutions to be assayed of the experimental group and the comparison group and the above multiple NMN samples of different concentrations were measured by a microplate reader (manufacturer: Thermo Fisher Scientific) for UV rays at 445 nm with an excitation wavelength of 382 nm, and corresponding readings were obtained. With the NMN concentration standard line made by the multiple NMN samples of different concentrations, the NMN content of the experimental group and the comparison group was converted by an inner difference method, as shown in FIG. 2.

Figure 2:
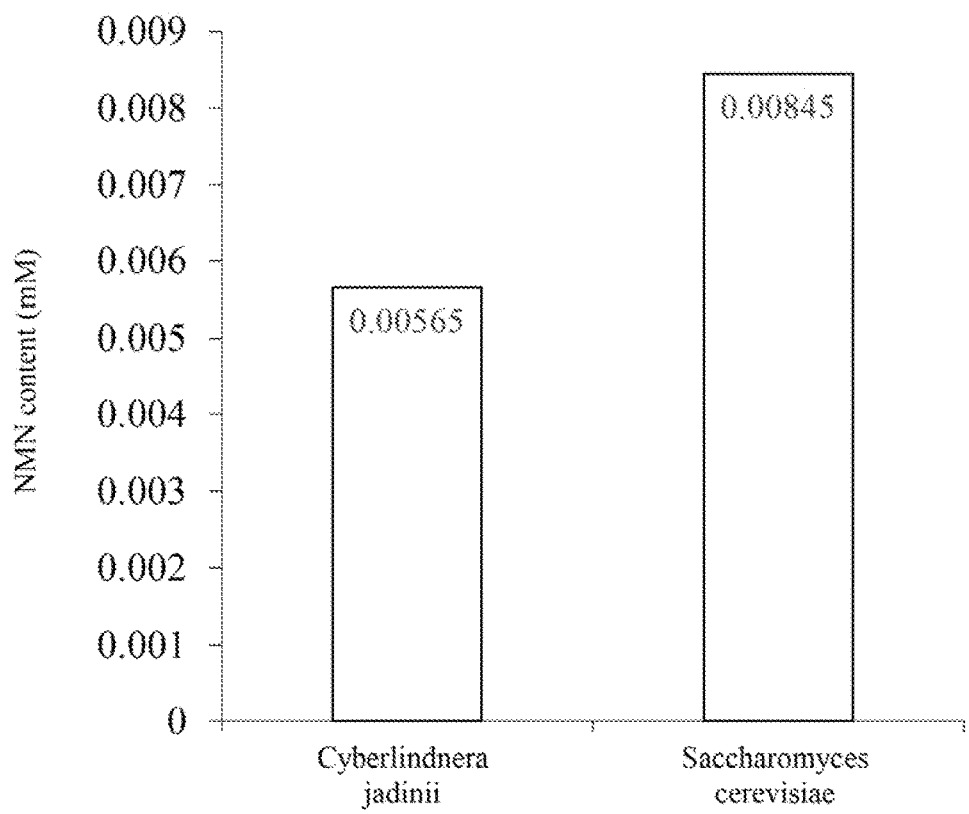
FIG. 2 is a graph showing the experimental result of NMN yield analysis under different strains.

Please refer to FIG. 2. The content of nicotinamide mononucleotide in the experimental group was 0.00845 mM, and the content of nicotinamide mononucleotide in the comparison group was 0.00565 mM. In other words, the content of nicotinamide mononucleotide in the yeast powder prepared from *Saccharomyces cerevisiae* in the experimental group was 1.5 times that of the comparison group.

It can thus be seen that the use of *Saccharomyces cerevisiae* for fermentation can increase the content of nicotinamide mononucleotide in the yeast powder.

Example 3. Fermentation Process: Fermentation Medium Test

Herein, the content of nicotinamide mononucleotide (NMN) in the yeast powder was used as a judgment index.

An experimental group was the yeast powder prepared in Example 1. The fermentation medium used included 99.6631% of basic medium, 0.1% of nicotinamide (NAM), 0.2% of tryptophan and 0.0369% of niacin. Components of the basic medium included 2.0% of yeast peptone GLS, 2.0% of yeast extract 902, 0.5% of potassium dihydrogen phosphate ($KH_2PO_4$), 0.5% of potassium hydrogen phosphate ($K_2HPO_4$), 0.05% of magnesium sulfate ($MgSO_4.7H_2O$), 10% of glucose, 0.17% of citric acid, 0.5% of sodium acetate, 0.016% of manganese gluconate, 0.1% of cysteine, 0.05% of an antifoaming agent and deionized distilled water (made up to 99.6631%).

Yeast powder of a comparison group was prepared according to the preparation process of Example 1 but the fermentation medium used in Example 1 was replaced. In other words, the difference from the preparation process of Example 1 was that the fermentation medium used in the preparation process of the comparison group was the basic medium, and components of the basic medium included 2.0% of yeast peptone GLS, 2.0% of yeast extract 902, 0.5% of potassium dihydrogen phosphate ($KH_2PO_4$), 0.5% of potassium hydrogen phosphate ($K_2HPO_4$), 0.05% of magnesium sulfate ($MgSO_4.7H_2O$), 10% of glucose, 0.17% of citric acid, 0.5% of sodium acetate, 0.016% of manganese gluconate, 0.1% of cysteine, 0.05% of an antifoaming agent and deionized distilled water (made up to 100%).

1 gram of yeast powder was taken from each of the experimental group and the comparison group and dissolved in 9 grams of water to form a yeast solution separately, and the yeast cells were disrupted with a cell disrupter (brand: Sunway Scientific Co., Ltd.) on ice. Then, the yeast solutions of the experimental group and the comparison group after the cell disruption treatment and a reaction solution were added to a 96-well plate separately, and reacted on ice for 2 minutes, and then 88% formic acid (a commercially available product) was added and reacted at 37° C. for another 10 minutes to obtain solutions to be assayed. Herein, the reaction solution included 20% acetophenone (a commercially available product) dissolved in DMSO, and 2M potassium hydroxide (a commercially available product).

Commercially available NMN (manufacturer: Wuxi Cima Science Co., Ltd.) was serially diluted into NMN samples with different concentrations in a range of 0.04 mM to 0.000625 mM, and 250 μL of each sample was added to a 96-well plate separately to facilitate subsequent production of an NMN concentration standard line, and the concentration was expressed in ppm instead.

Then, the solutions to be assayed of the experimental group and the comparison group and the above multiple NMN samples of different concentrations were measured by a microplate reader (manufacturer: Thermo Fisher Scientific) for UV rays at 445 nm with an excitation wavelength of 382 nm, and corresponding readings were obtained. With the NMN concentration standard line made by the multiple NMN samples of different concentrations, the NMN content of the experimental group and the comparison group was converted by an inner difference method, as shown in FIG. 3.

Figure 3:
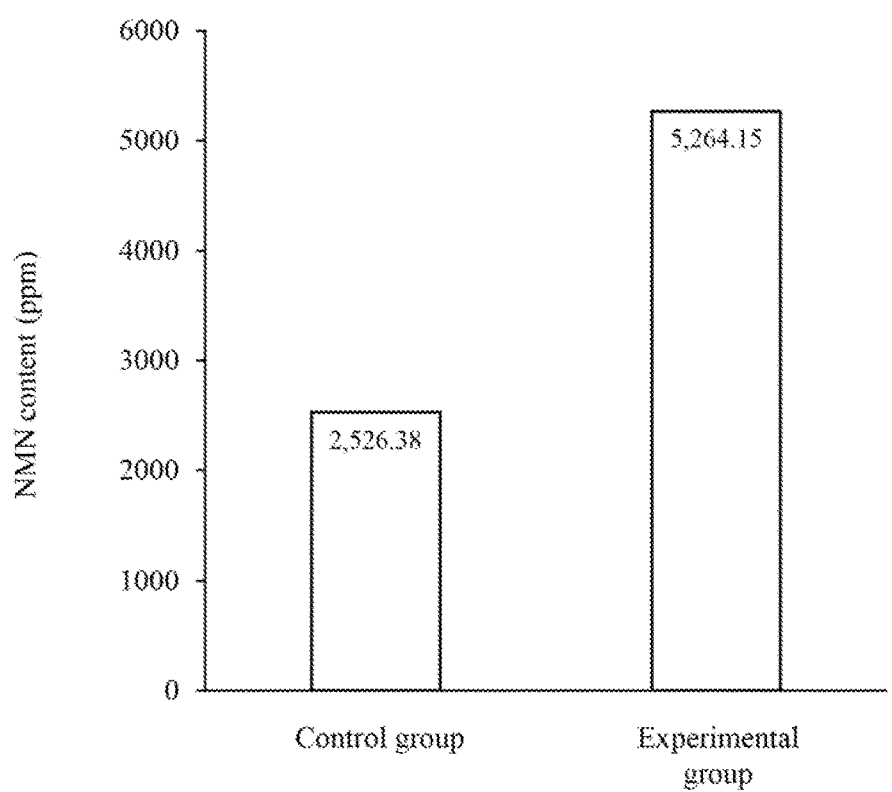
FIG. 3 is a graph showing the experimental result of NMN yield analysis under different fermentation medium components.

Please refer to FIG. 3. The content of nicotinamide mononucleotide in the experimental group was 5264.15 ppm, and the content of nicotinamide mononucleotide in the comparison group was 2526.38 ppm. In other words, the content of nicotinamide mononucleotide in the yeast powder prepared from *Saccharomyces cerevisiae* in the experimental group was 2.1 times that of the comparison group.

It can thus be seen that using the fermentation medium containing nicotinamide (NAM), tryptophan and Niacin for fermentation can increase the content of nicotinamide mononucleotide in the yeast powder.

Example 4: Fermentation Process: Fermentation Medium Test (Plant Extracts and Compounds)

Herein, the nicotinamide mononucleotide (NMN) contained in the yeast powder was used as a judgment index, and the content of nicotinamide mononucleotide contained in the yeast of Example 1 was used as an index basis to determine a relative content ratio of nicotinamide mononucleotide in each group (hereinafter referred to as NMN relative content ratio).

A control group was the yeast powder prepared in Example 1. Components of the fermentation medium used included 99.6631% of basic medium, 0.1% of nicotinamide, 0.2% of tryptophan and 0.0369% of niacin. Components of the basic medium are the same as those described in Example 1 and Example 2, and will not be repeated here.

Experimental groups were a *Musa* spp. peel extract group, an *Aronia melanocarpa* extract group and a *Solanum lycopersicum* extract group separately. The yeast powder of the experimental groups was prepared according to the preparation process of Example 1 but the fermentation medium used in Example 1 was replaced. In other words, the difference from the preparation process of Example 1 was that the fermentation medium used in the preparation process of the experimental groups contained 0.1% of nicotinamide, 0.2% of tryptophan, 0.0369% of niacin, and a corresponding percentage of plant extracts. In addition, the plant extract used in the *Musa* spp. peel extract group was 0.05% of *Musa* spp. peel extract, the plant extract used in the *Aronia melanocarpa* extract group was 0.085% of *Aronia melanocarpa* extract, the plant extract used in the *Solanum lycopersicum* extract group was 0.05% of *Solanum lycopersicum* extract, and the rest was supplemented to 100% with the basic medium.

Herein, the *Musa* spp. peel extract used in the *Musa* spp. peel extract group was prepared by separating the peel from pulp of *Musa* spp., and performing the following operations on the *Musa* spp. peel to provide the *Musa* spp. peel extract: 1) the *Musa* spp. peel was mixed with an extraction solvent (a volume ratio of the *Musa* spp. peel to the extraction solvent was 1:6; the extraction solvent was provided according to a volume ratio of citric acid:water=1:100), and extraction was performed at 85° C. for 0.5 hours to provide a crude extract; 2) the crude extract of step 1 was centrifuged at 5000 rpm. for 10 minutes, and a supernatant was taken and filtered with a 400-mesh filter screen to provide a filtrate; 3) at 55+/−5° C., the filtrate of step 2 was concentrated under reduced pressure to provide a concentrated extract; and 4) the concentrated extract of step 3 was freeze-dried to provide a dried product (i.e., the *Musa* spp. peel extract). The *Aronia melanocarpa* extract used in the *Aronia melanocarpa* extract group was prepared by cutting *Aronia melanocarpa* fruits into pieces and homogenizing the pieces to form an *Aronia melanocarpa* homogenate, and then extracting the *Aronia melanocarpa* homogenate with water at 40° C. to 60° C. for 0.5 hours to 2 hours, wherein the liquid-solid ratio of the water to the *Aronia melanocarpa* homogenate was (5-20): (1-5). The *Solanum lycopersicum* extract used in the *Solanum lycopersicum* extract group was prepared by cutting *Solanum lycopersicum* (kumato) into pieces and homogenizing the pieces to form a *Solanum lycopersicum* homogenate, and then extracting the *Solanum lycopersicum* homogenate with water at 40° C. to 60° C. for 0.5 hours to 2 hours, wherein a liquid-solid ratio of the water to the *Solanum lycopersicum* homogenate was (5-20): (1-5).

Control groups were a tannic acid group, a licorice extract group and a *Passiflora* spp. extract group. The yeast powder of the control groups was prepared according to the preparation process of Example 1 but the fermentation medium used in Example 1 was replaced. In other words, the difference from the preparation process of Example 1 was that the fermentation medium used in the preparation process of the control groups contained 0.1% of nicotinamide, 0.2% of tryptophan, 0.0369% of niacin, and a corresponding percentage of plant extracts or compounds. In addition, the compound used in the tannic acid group was 5 µM tannic acid (manufacturer: Sigma-Aldrich), the plant extract used in the licorice extract group was 0.5% of licorice extract, the plant extract used in the *Passiflora* spp. extract group was 4% of *Passiflora* spp. extract, and the rest was supplemented to 100% with the basic medium.

Herein, the licorice extract used in the licorice extract group was prepared by chopping licorice, mixing the chopped licorice with an aqueous solution containing 0.5% to 2% of citric acid separately at a solid to liquid ratio of 1:2 to 1:10, placing the mixed solution at 50° C. to 100° C. to perform extraction for 30 minutes to 120 minutes, cooling the extract to room temperature and filtering the extract with a 200-micron filter to obtain the licorice extract. The *Passiflora* spp. extract used in the *Passiflora* spp. extract group was prepared by washing and drying *Passiflora edulis* (*Passiflora* spp. plant) seeds, then coarsely crushing the *Passiflora edulis* seeds by a homogenizer to form a *Passiflora* spp. seed homogenate, mixing the *Passiflora* spp. seed homogenate with water at a material-to-water ratio (by weight) of 1:5, and performing extraction at 55° C. for 1 hour and then at 85° C. for another 1 hour.

1 gram of yeast powder was taken from each of the control group, the experimental groups and the comparison groups and dissolved in 9 grams of water to form a yeast solution separately, and the yeast cells were disrupted with a cell disrupter (brand: Sunway Scientific Co., Ltd.) on ice. Then, the yeast solutions of the control group, the experimental groups and the comparison groups after the cell disruption treatment and a reaction solution were added to a %-well plate separately, and reacted on ice for 2 minutes, and then 88% formic acid (a commercially available product) was added and reacted at 37° C. for another 10 minutes to obtain solutions to be assayed. Herein, the reaction solution included 20% acetophenone (a commercially available product) dissolved in DMSO, and 2M potassium hydroxide (a commercially available product).

Commercially available NMN (manufacturer: Wuxi Cima Science Co., Ltd.) was serially diluted into NMN samples with different concentrations in a range of 0.04 mM to 0.000625 mM, and 250 μL of each sample was added to a 96-well plate separately to facilitate subsequent production of an NMN concentration standard line.

Then, the solutions to be assayed of the control group, the experimental groups and the comparison groups and the above multiple NMN samples of different concentrations were measured by a microplate reader (manufacturer: Thermo Fisher Scientific) for UV rays at 445 nm with an excitation wavelength of 382 nm, and corresponding readings were obtained. With the NMN concentration standard line made by the multiple NMN samples of different concentrations, the NMN content of the control group, the experimental groups and the comparison groups was converted by an inner difference method. Herein, the reading of the control group was regarded as 1 to convert the relative content ratio of NMN of the experimental groups and the comparison groups, as shown in FIG. 4.

Figure 4:
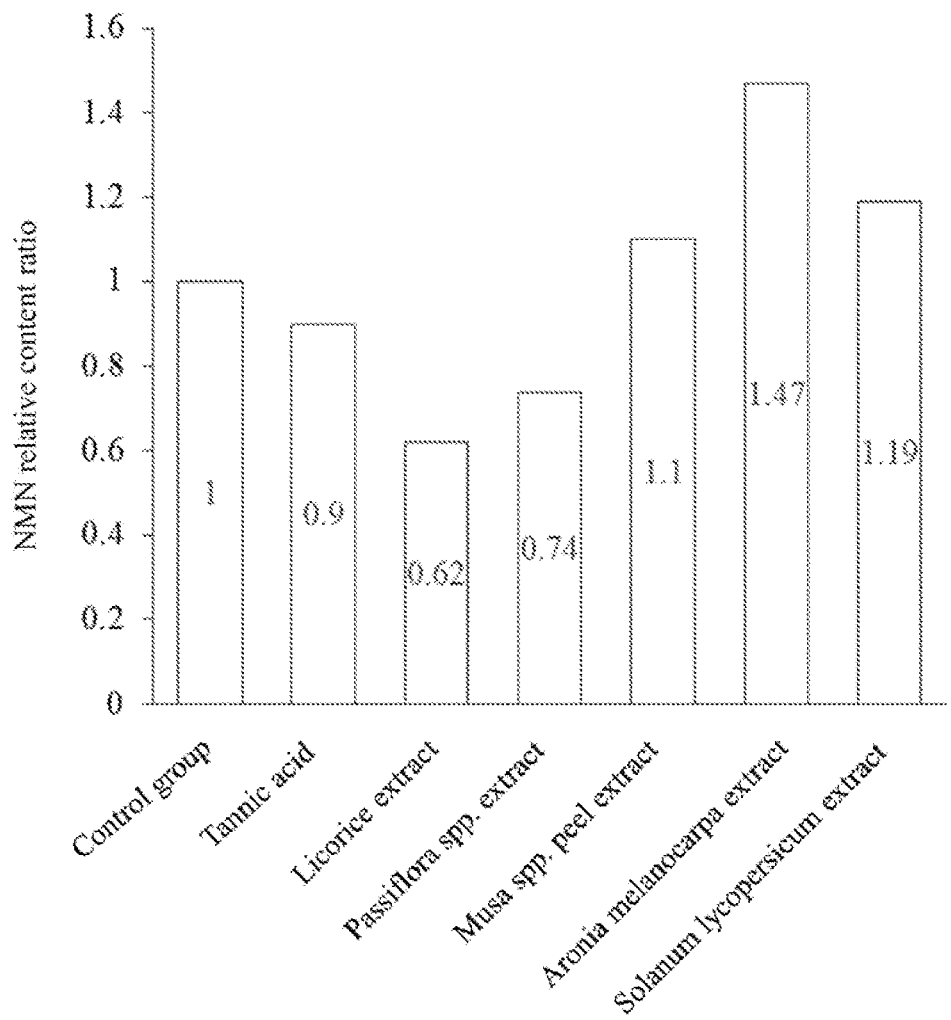
FIG. 4 is a graph showing the experimental result of NMN yield analysis under plant extracts and compounds.

Please refer to FIG. 4. The relative content ratio of NMN of the control group was regarded as 1.0. Compared with the control group, in the comparison groups, the relative content ratio of NMN of the tannic acid group was 0.9, the relative content ratio of NMN in the licorice extract group was 0.62, and the relative content ratio of NMN of the *Passiflora* spp. extract group was 0.74. Compared with the control group, in the experimental groups, the relative content ratio of NMN of the *Musa* spp. peel extract group was 1.1, the relative content ratio of NMN of the *Aronia melanocarpa* extract group was 1.47, and the relative content ratio of NMN of the *Solanum lycopersicum* extract group was 1.19. In other words, compared with the control group and the comparison groups, the yeast powder of each group prepared by adding 0.05% of *Musa* spp. peel extract, 0.085% of *Aronia melanocarpa* extract and 0.05% of *Solanum lycopersicum* extract to the fermentation medium contained a higher content of nicotinamide mononucleotide. Moreover, when 0.085% of *Aronia melanocarpa* extract was added to the fermentation medium, the obtained yeast powder could contain nearly 1.5 times the content of nicotinamide mononucleotide. In addition, it can be seen from the experimental results of the comparison groups that not all plant extracts can increase the content of nicotinamide mononucleotide in the yeast powder.

It can thus be seen that when the *Musa* spp. peel extract, the *Aronia melanocarpa* extract, and the *Solanum lycopersicum* extract were added to the fermentation medium, the content of nicotinamide mononucleotide in the yeast powder prepared therefrom could be increased.

Example 5: Cell Experiment: Inhibition of ROS Generation (Hydrogen Peroxide Treatment)

Herein, a fluorescent probe DCFH-DA combined with flow cytometry was used to measure the changes in the content of reactive oxygen species (ROS) in mouse brain neuroblastoma cells (Neuro2a) treated with yeast powder containing nicotinamide mononucleotide (NMN).

A medium used was a DMEM medium (Dulbecco's Modified Eagle Medium; brand: Gibco) supplemented with 10 vol % of fetal bovine serum (FBS; brand: Gibco) and 1 vol % of penicillin/streptomycin (brand: Gibco), hereinafter referred to as a cell medium. A DCFH-DA solution used was a reaction solution prepared by dissolving 2,7-dichloro-dihydro-fluorescein diacetate (DCFH-DA, product code SI-D6883, purchased from Sigma) in dimethyl sulfoxide (DMSO, purchased from Sigma, product code SI-D6883-50MG).

First, $2\times10^5$ mouse neuroblastoma cells (ATCC CCL-131; hereinafter referred to as Neuro2a cells) were added into a six-well cell culture plate containing 2 mL of the above cell medium per well, and cultured at 37° C. for 24 hours.

After the Neuro2a cells in each well were attached to the bottom of the six-well cell culture plate, the Neuro2a cells were divided into a blank group, a control group, a comparison group, and an experimental group. Then, the cell medium of each group was replaced with an experimental medium, and then the experimental medium was placed at 37° C. for continuous culture for 24 hours. The experimental medium of each of the blank group and the control group was a simple cell medium. The experimental medium of the comparison group was a cell medium supplemented with 10 μL of chemically synthesized nicotinamide mononucleotide (manufacturer: Sigma-Aldrich) with a concentration of 200 mM. The experimental medium of the experimental group was a cell medium containing 0.25 vol % of the yeast powder rich in NMN prepared in Example 1.

Next, 2 μL of 5 μg/mL DCFH-DA solution was added to each well of the experimental medium for post-treatment of the Neuro2a cells for 15 minutes in each group. After the reaction in the DCFH-DA solution, 10 μL of 200 mM hydrogen peroxide (Sigma-Aldrich) was added to the experimental medium of each group, and reacted at 37° C. for 1 hour.

Then, after the experimental medium of each group was removed, the Neuro2a cells of each group were rinsed twice with 1 mL of 1×PBS solution. Then, 200 IL of trypsin was added to each well for reaction for 5 minutes. After the reaction, 1 mL of cell medium was added to each well to stop the reaction. The Neuro2a cells and the cell medium in each well were collected into a corresponding 1.5 mL microcentrifuge tube, and the microcentrifuge tube containing the Neuro2a cells and the cell medium was centrifuged at 400×g for 5 minutes. After centrifugation, a supernatant was removed from the microcentrifuge tube of each group, the pellet of Neuro2a cells was re-dissolved with a 1×PBS solution, and centrifuged at 400×g for 5 minutes. After centrifugation, a supernatant was removed from the microcentrifuge tube of each group, and the Neuro2a cells were resuspended in the dark with 200 μL of 1×PBS solution per centrifuge tube to obtain cell solutions to be assayed of each group.

Figure 5:
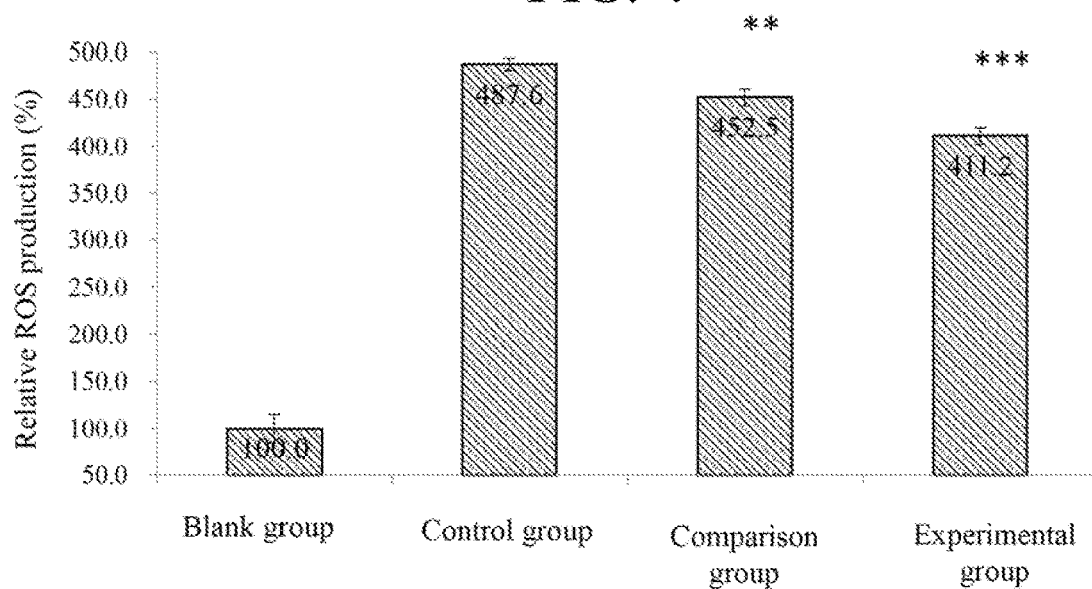
FIG. 5 is a graph showing the experimental result of the amount of relative ROS generated.

Flow cytometry (manufacturer: Beckman; Catalog No. 660519) was used to detect a fluorescence signal of DCFH-DA in the cell solutions to be assayed in each group. The excitation wavelength of fluorescence detection used was 450 nm to 490 nm, and the emission wavelength was 510 nm to 550 nm. Since DCFH-DA will first be hydrolyzed to DCFH (dichloro-dihydro-fluorescein) after entering the Neuro2a cells, and then oxidized by reactive oxygen species (ROS) into DCF (dichloro-fluorescein) that emits green fluorescence, the fluorescence intensity of the Neuro2a cells treated with the DCFH-DA can reflect the content of reactive oxygen species (ROS) in the Neuro2a cells, and from this, the ratio of the number of cells with highly expressed reactive oxygen species (ROS) in the Neuro2a cells to the number of original cells can be known. Since the experiment was performed twice, the measurement results of the two repeated experiments in each group were averaged to obtain an average value, then the average value of the blank group was regarded as 100% of the relative ROS production, and the average values of the control group, the comparison group and the experimental group were converted into the relative ROS production, as shown in FIG. 5. In addition, the expression of the Neuro2a cells in each group was observed with a fluorescence microscope (Beckman).

Please refer to FIG. 5. The cells in the blank group were not treated with hydrogen peroxide, and their relative ROS production was regarded as 100% for reference. Under a fluorescence microscope, the Neuro2a cells in the blank group showed blue, indicating that no cell oxidative stress is induced. After the control group was treated with hydrogen peroxide, the relative ROS production (high fluorescence expression) was significantly increased to 487.6% compared to the blank group, and under a fluorescence microscope, the Neuro2a cells showed fluorescent green, indicating that hydrogen peroxide treatment does cause ROS production in the cells, which in turn causes subsequent damage to the Neuro2a cells. After the comparison group was treated with hydrogen peroxide, the relative ROS production was increased to 452.5% compared with the blank group, but was decreased by 35.1% compared with the control group. In addition, under a fluorescence microscope, the Neuro2a cells in the control group showed a blue-green staggered but greenish color, indicating that the chemically synthesized nicotinamide mononucleotide in the cell medium slightly assisted the Neuro2a cells to resist the cell oxidative stress caused by hydrogen peroxide. After the experimental group was treated with hydrogen peroxide, the relative ROS production was increased to 411.2% compared with the blank group, but was decreased by 76.4% compared with the control group. In addition, under a fluorescence microscope, the Neuro2a cells in the experimental group showed a mainly blue but still a little green color, indicating that the natural nicotinamide mononucleotide in the cell medium can effectively reduce the production or accumulation of reactive oxygen species (ROS) in cells, and thus better assist the Neuro2a cells in resisting cell oxidative stress caused by hydrogen peroxide. Moreover, compared with the comparison group, the relative ROS production of the Neuro2a cells in the experimental group was decreased significantly (about 2.17 times), indicating that the natural nicotinamide mononucleotide in the yeast powder is more effective in reducing the production or accumulation of reactive oxygen species (ROS) in cells and helping cells resist ROS damage than the chemically synthesized nicotinamide mononucleotide, and has antioxidation and antiaging capabilities.

In other words, the yeast powder rich in nicotinamide mononucleotide can be used as a scavenger of reactive oxygen species. That is, the yeast powder rich in nicotinamide mononucleotide can reduce the oxidative damage of cells caused by the reactive oxygen species (ROS) by reducing the content of the reactive oxygen species in cells.

Based on this, when a subject takes the yeast powder rich in nicotinamide mononucleotide, the yeast powder can more effectively resist the damage of ROS, and then achieve the effects of antioxidation and antiaging.

Example 6: Cell Experiment: Mitochondrial Activity

Herein, flow cytometry was used to assess the changes in the mitochondrial activity in mouse brain neuroblastoma cells (Neuro2a) treated with yeast powder containing nicotinamide mononucleotide (NMN).

A medium used was a DMEM medium (Dulbecco's Modified Eagle Medium; brand: Gibco) supplemented with 10 vol % of fetal bovine serum (FBS; brand: Gibco) and 1 vol % of penicillin/streptomycin (brand: Gibco), hereinafter referred to as a cell medium. A mitochondrial activity test method used was to use a mitochondrial membrane potential detection kit (BD™ MitoScreen (JC-1) kit, model 551302) to measure the mitochondrial membrane potential and perform mitochondrial activity analysis. The mitochondrial membrane potential detection kit included a JC-1 stain (freeze-dried) and a 10×assay buffer. Before use, the 10×assay buffer was diluted 10 times with 1×PBS to form a 1×assay buffer. 130 µL of DMSO was added to the JC-1 stain (freeze-dried) to form a JC-1 stock solution. Then, the JC-1 stock solution was diluted with the 1×assay buffer to form a JC-1 working solution (JC-1 mitochondrial specific stain). The dilution ratio of the JC-1 stock solution to the 1×assay buffer was 1:100.

First, $1 \times 10^5$ mouse neuroblastoma cells (ATCC CCL-131; hereinafter referred to as Neuro2a cells) were added into a six-well cell culture plate containing 2 mL of the above cell medium per well, and cultured at 37° C. for 24 hours.

After the Neuro2a cells in each well were attached to the bottom of the six-well cell culture plate, the Neuro2a cells were divided into an experimental group, a comparison group, and a control group. Then, the cell medium of each group was replaced with an experimental medium, and then the experimental medium was placed at 37° C. for continuous culture for 24 hours. The experimental medium of the experimental group was a cell medium supplemented with 0.25 vol % of the yeast powder prepared in Example 1. The experimental medium of the comparison group was a cell medium supplemented with 0.25 vol % of chemically synthesized nicotinamide mononucleotide (manufacturer: Sigma-Aldrich). The experimental medium of the control group was a simple cell medium.

Then, after the experimental medium of each group was removed, the Neuro2a cells of each group were rinsed twice with 1 mL of 1×DPBS solution. Then, 200 µL of trypsin was added to each well for reaction for 5 minutes. After the reaction, 1 mL of cell medium was added to each well to stop the reaction. The Neuro2a cells and the cell medium in each well were collected into a corresponding 1.5 mL microcentrifuge tube, and the microcentrifuge tube containing the Neuro2a cells and the cell medium was centrifuged at 400×g for 5 minutes. After centrifugation, a supernatant was removed from the microcentrifuge tube of each group, the pellet of Neuro2a cells was re-dissolved with a 1×DPBS solution, and centrifuged at 400×g for 5 minutes. After centrifugation, a supernatant was removed from the microcentrifuge tube of each group, and 100 µL of JC-1 working solution was added to each microcentrifuge tube, so that the pellet of Neuro2a cells was uniformly mixed with the JC-1 working solution, and then allowed to stand for 15 minutes in the dark. After standing for 15 minutes, the microcentrifuge tube containing the Neuro2a cells and the JC-1 working solution was centrifuged at 400×g for 5 minutes. Next, a supernatant was removed from the microcentrifuge tube of each group, and a 1×assay buffer was added to re-dissolve the pellet of the Neuro2a cells, and then centrifuged at 400×g for 5 minutes, and the operation was repeated twice. A supernatant was removed from the microcentrifuge tube of each group, and the pellet of the Neuro2a cells was resuspended with a 1×DPBS solution containing 2 vol % fetal bovine serum to obtain the cell solutions to be assayed.

Figure 6:
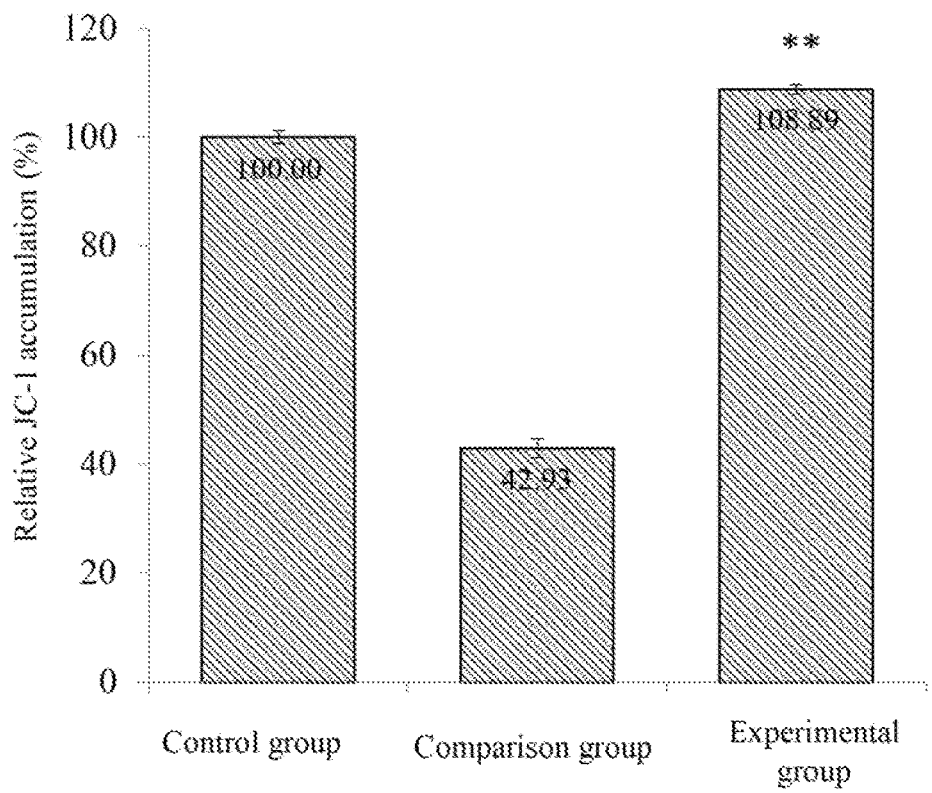
FIG. 6 is a graph showing the experimental result of a mitochondrial activity test.

Flow cytometry (manufacturer: Beckman, Catalog No. 660519) was used to measure the membrane potential of the mitochondria of the cells in the cell solution to be assayed in each group for the analysis of the mitochondrial activity. The wavelength of excitation light set by the flow cytometry was 488 nm, and the wavelength of scattered light was 527 nm and 590 nm. Since the experiment was performed thrice, the results of three repeated experiments in each group were averaged to obtain an average value, then the average value of the control group was regarded as 100% of the relative JC-1 accumulation, and the average relative JC-1 accumulations of the experimental group and the comparison group were obtained by conversion, as shown in FIG. 6. In FIG. 6, "**" represents that the p-value is less than 0.01 when compared with the control group. In addition, the mitochondrial expression of the Neuro2a cells in each group was observed with a fluorescence microscope (Beckman). Green fluorescence represents non-activated mitochondria and red fluorescence represents activated mitochondria.

Please refer to FIG. 6. The relative JC-1 accumulation of the control group was 100%. Under a fluorescence microscope, the mitochondria in the Neuro2a cells of the control group showed interlaced red and green fluorescence, and most fluorescence was green fluorescence, indicating that the mitochondria in the Neuro2a cells in the control group were partially activated but most cells were in an inactivated state. The relative JC-1 accumulation of the comparison group was 42.93%, and under a fluorescence microscope, the mitochondria in the Neuro2a cells in the comparison group showed mainly green fluorescence, indicating that most of the mitochondria in the Neuro2a cells of the comparison group were in an inactivated state. The relative JC-1 accumulation of the experimental group was 108.89%, and under a fluorescence microscope, the mitochondria in the Neuro2a cells in the experimental group showed mainly red fluorescence, indicating that most of the mitochondria in the Neuro2a cells of the experimental group were in an activated state. In other words, compared with the comparison group, the mitochondrial activity of the Neuro2a cells in the experimental group was significantly improved (by about 1.09 times), indicating that the yeast powder rich in nicotinamide mononucleotide can enhance the mitochondrial activity of nerve cells and achieve the effect of enhancing nerve cell activity. In addition, from FIG. 6, it can be seen that the chemically synthesized nicotinamide mononucleotide cannot activate the mitochondrial activity of nerve cells.

Based on this, when a subject takes the yeast powder rich in nicotinamide mononucleotide, the yeast powder can more effectively enhance the mitochondrial activity of nerve cells, and achieve the effects of enhancing nerve cell activity and antiaging.

Example 7: Cell Experiment: Antiaging-Related Genes

Herein, the tested antiaging-related genes are antiaging genes including CCT5 gene (Gene ID: 22948), CCT6A gene (Gene ID: 908), CCT7 gene (Gene ID: 10574), CCT8 gene (Gene ID: 10694), PARP2 gene (Gene ID: 10038), Parkin gene (Gene ID: 5071), Atg1 gene (Gene ID: 8408), Arg8 gene (Gene ID: 11345), FOX) gene (Gene ID: 2308), SIRT1 gene (Gene ID: 23411), NADSYN gene (Gene ID: 55191), and MRPS3 gene (Gene ID: 64969).

A medium used was an X-VIVO™ 15 serum-free hematopoietic cell medium (manufacturer: Lonza; product No.: 04-418Q) supplemented with 10 vol % of fetal bovine serum (FBS; brand: Gibco) and 1 vol % of penicillin/streptomycin (brand: Gibco), hereinafter referred to as a cell medium.

First, $1 \times 10^6$ human peripheral blood mononuclear cells (PBMC, isolated from human; purchased from ATCC, model No. PCS-200-010™; hereinafter referred to as PBMC cells) were taken into a six-well cell culture plate containing 2 mL of cell medium per well, and cultured at 37° C. for 24 hours.

The PBMC cells were divided into an experimental group, a comparison group and a control group. The cell medium of each group was removed and replaced with 2 mL of experimental medium per well, and then placed at 37° C. for continuous culture for 24 hours. The experimental medium of the experimental group was a cell medium supplemented with 0.25 vol % of the yeast powder prepared in Example 1. The experimental medium of the comparison group was a cell medium supplemented with 0.25 vol % of chemically synthesized nicotinamide mononucleotide (manufacturer: Sigma-Aldrich). The experimental medium of the control group was a simple cell medium.

PBMC cells were collected from each group, and RNA of each group was extracted with an RNA extraction reagent kit (purchased from Geneaid, Taiwan, China, Lot No. FC24015-G). Then, 1000 ng of RNA of each group was taken as a template, and the RNA was reversely transcribed into the corresponding cDNA by SuperScript® III reverse transcriptase (purchased from Invitrogene, USA, product No. 18080-051). Then, by using an ABI StepOnePlus™ Real-Time PCR system (Thermo Fisher Scientific Company, USA), KAPA SYBR FAST (purchased from Sigma Company, USA, No. 38220000000) and primers of Table 1 (SEQ ID NO: 1 to SEQ ID NO: 24), a quantitative real-time reverse transcription polymerase chain reaction was performed on the cDNA of each group to observe the expression levels of antiaging-related genes in PBMC cells. Instrument setting conditions for the quantitative real-time reverse transcription polymerase chain reaction were reaction at 95° C. for 20 seconds, then reaction at 95° C. for 3 seconds, and reaction at 60° C. for 30 seconds, cycles were repeated, and a 2-ΔCt method was used for gene quantification, as shown in FIG. 7 to FIG. 10. Herein, the quantitative real-time reverse transcription polymerase chain reaction of the cDNA can indirectly quantify an mRNA expression level of a gene, and then infer the expression level of protein encoded by the gene.

It should be noted that the gene expression in FIG. 7 to FIG. 10 was presented in terms of relative expression, an STDEV formula of Excel software was used to calculate standard deviation, and the statistically significant difference among the groups was statistically analyzed by a student t-test. In FIG. 7 to FIG. 10, "*" represents that the p value is less than 0.05 when compared with the control group, "" represents that the p value is less than 0.01 when compared with the control group, and "*" represents that the p value is less than 0.001 when compared with the control group.

TABLE 1

| Target gene | Primer name | Sequence NO. | Sequence | Primer length |
|---|---|---|---|---|
| PARP2 | PARP2-F | SEQ ID NO: 1 | AGCAAGATGAATCTGTGAAGGC | 22 |
|  | PARP2-R | SEQ ID NO: 2 | CACTGAAGTTCCTCTGGGCA | 20 |
| CCT5 | CCT5-F | SEQ ID NO: 3 | ATAAATGTGAGGCTGAATC | 19 |
|  | CCT5-R | SEQ ID NO: 4 | ACTTGTCACTTGTGGCAC | 18 |

TABLE 1-continued

| Target gene | Primer name | Sequence NO. | Sequence | Primer length |
|---|---|---|---|---|
| CCT6A | CCT6A-F | SEQ ID NO: 5 | TGTGTATCTTAATCCAGACTC | 21 |
|  | CCT6A-R | SEQ ID NO: 6 | CGTTTCACCTAAGAGTTGTC | 20 |
| CCT7 | CCT7-F | SEQ ID NO: 7 | GTGGCATGGACAAGCTTATTGTAG | 24 |
|  | CCT7-R | SEQ ID NO: 8 | CAGAATTGTGGCCCCATCA | 19 |
| CCT8 | CCT8-F | SEQ ID NO: 9 | ACCCGGAGGTGGAGCAA | 17 |
|  | CCT8-R | SEQ ID NO: 10 | GGACATGTCTCTCCATATGATGTGA | 25 |
| Parkin | Parkin-F | SEQ ID NO: 11 | GCAGAGACCGTGGAGAAAAG | 20 |
|  | Parkin-R | SEQ ID NO: 12 | CTTTTCTCCACGGTCTCTGC | 20 |
| Atg1 | Atg1-F | SEQ ID NO: 13 | CAGGAGGACGAGAACACGGTGTC | 23 |
|  | Atg1-R | SEQ ID NO: 14 | GGAAGGTTCTTTGGCACCAGCAC | 23 |
| Arg8 | Atg8-F | SEQ ID NO: 15 | CCGCAGTAGGTGGCAAAGTA | 20 |
|  | Atg8-R | SEQ ID NO: 16 | GGAGTCGGAGAGGATTGCTG | 20 |
| FOXO | FOXO-F | SEQ ID NO: 17 | CGGACAAACGGCTCACTCT | 19 |
|  | FOXO-R | SEQ ID NO: 18 | GGACCCGCATGAATCGACTAT | 21 |
| SIRT1 | SIRT1-F | SEQ ID NO: 19 | TGCTGGCCTAATAGAGTGGCA | 21 |
|  | SIRT1-R | SEQ ID NO: 20 | CTCAGCGCCATGGAAAATGT | 20 |
| NADSYN | NADSYN-F | SEQ ID NO: 21 | GCAAAATGTGCAGGCTCGAA | 20 |
|  | NADSYN-R | SEQ ID NO: 22 | GCACTGGAGCAGTCGTACTT | 20 |
| MRPS5 | MRPS5-F | SEQ ID NO: 23 | GTCCGGACAGTCCCTCAC | 18 |
|  | MRPS5-R | SEQ ID NO: 24 | CCCAATAAATGACCTGCCGTC | 21 |

In Table 1, F represents a forward primer, and R represents a reverse primer.

Figure 7:
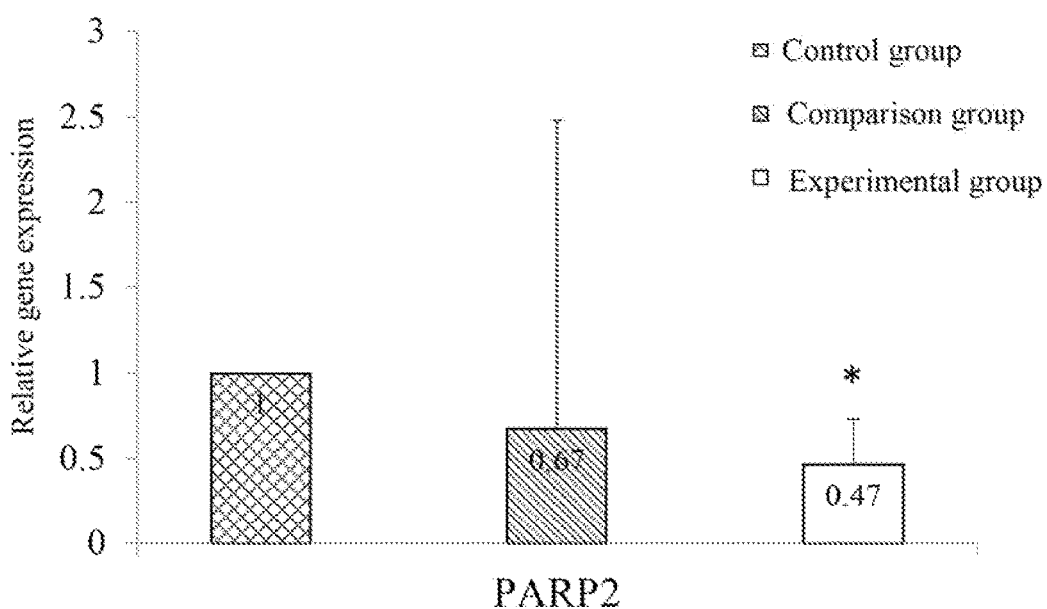
FIG. 7 is a graph showing the experimental result of the relative expression level of the PARP2 gene.

Please refer to FIG. 7. The relative expression of each group of PARP2 genes in the control group was regarded as 1.00 (that is, the expression level of each group of genes in the control group was 100%). Compared with the control group, the relative expression of the PARP2 gene in the experimental group was 0.47, while the relative expression of the PARP2 gene in the comparison group was 0.67. Moreover, compared with the comparison group, the expression level of the PARP2 gene in the experimental group was significantly reduced, indicating that the yeast powder rich in naturally synthesized nicotinamide mononucleotide can inhibit the expression level of the PARP2 gene more effectively than the chemically synthesized nicotinamide mononucleotide. In other words, when the subject takes the yeast powder rich in naturally synthesized nicotinamide mononucleotide, the yeast powder can effectively inhibit the expression level of the PARP2 gene, thereby promoting cell rejuvenation and telomerase activity, and achieving the antiaging function.

Figure 8:
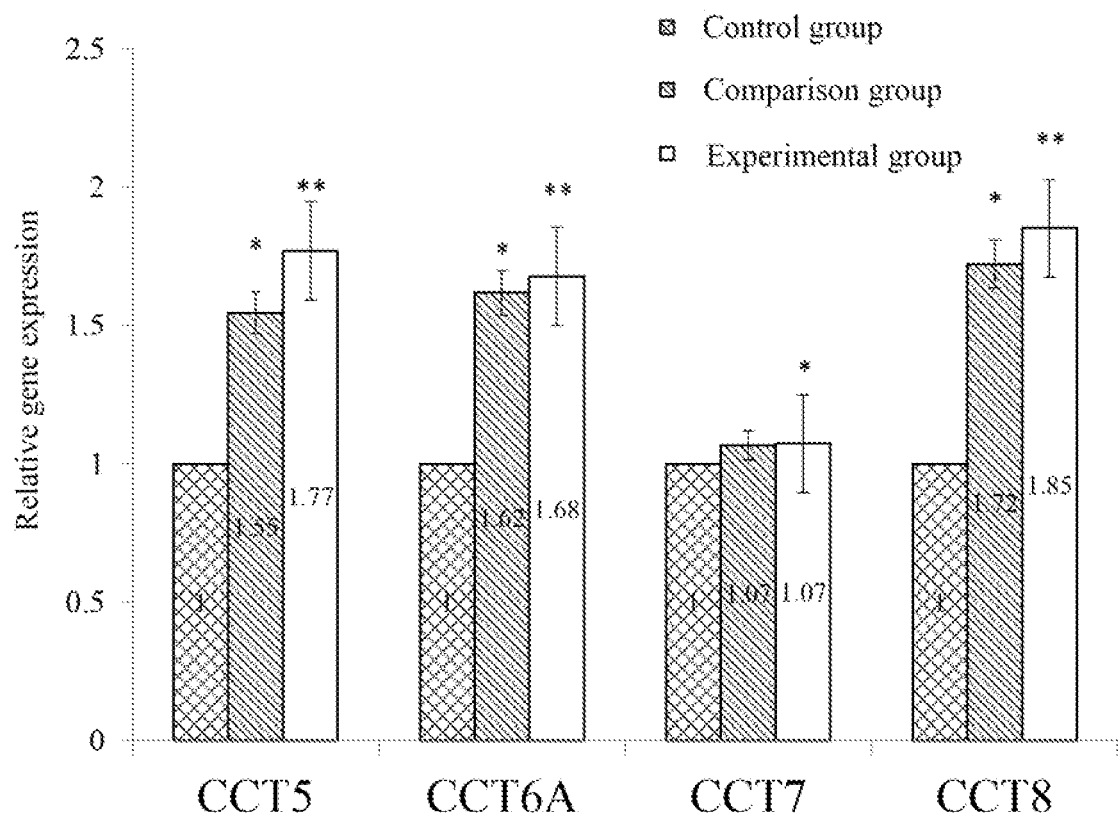
FIG. 8 is a graph showing the experimental result of the relative expression levels of CCT-related genes.

Please refer to FIG. 8. The relative expression of each group of CCT genes in the control group was regarded as 1.00 (that is, the expression level of each group of CCT genes in the control group was 100%). Compared with the control group, in the experimental group, the relative expression of the CCT5 gene was 1.77, the relative expression of the CCT6A gene was 1.68, the relative expression of the CCT7 gene was 1.0736 (marked as 1.07 in FIG. 8), and the relative expression of the CCT8 gene was 1.85. In the comparison group, the relative expression of the CCT5 gene was 1.55, the relative expression of the C7T6A gene was 1.62, the relative expression of the (17 gene was 1.0672 (marked as 1.07 in FIG. 8), and the relative expression of the CCT8 gene was 1.72. It can thus be seen that the expression levels of the CCT genes in the experimental group were significantly higher than the expression levels of the CCT genes in the comparison group, indicating that the yeast powder rich in the naturally synthesized nicotinamide mononucleotide can improve the expression of the CCT genes more effectively than the chemically synthesized nicotinamide mononucleotide, thereby rejuvenating mature cells to young cells and achieving an antiaging effect. In other words, when the subject takes the yeast powder rich in naturally synthesized nicotinamide mononucleotide, the yeast powder can effectively improve the expression levels of the CCT genes, thereby promoting cell rejuvenation, and achieving the antiaging function.

Figure 9:
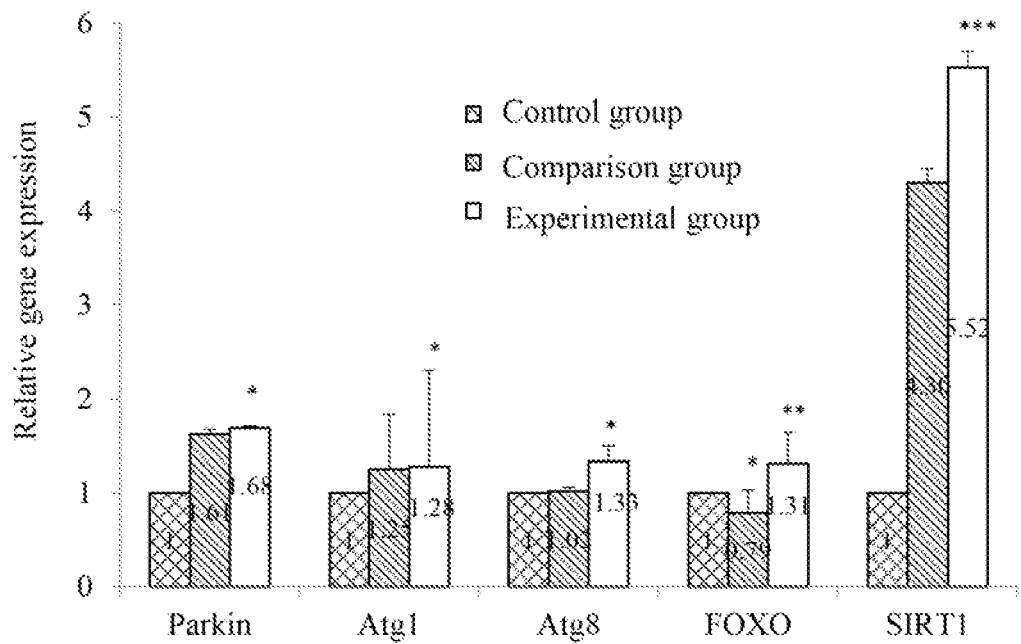
FIG. 9 is a graph showing the experimental result of the relative expression levels of antiaging-related genes.

Please refer to FIG. 9. The relative expression of each group of antiaging-related genes (herein, referring to the Parkin gene, the Atg1 gene, the Atg8 gene, the FOXO gene, and the SIRT1 gene) in the control group is regarded as 1.00 (that is, the expression level of each group of genes in the control group is 100%). Compared with the control group, the relative expression of the Parkin gene in the experimental group was 1.68, the relative expression of the Atg1 gene was 1.28, the relative expression of the Atg8 gene was 1.33, the relative expression of the FOXO gene was 1.31, and the relative expression of the SIRT1 gene was 5.52; while in the comparison group, the relative expression of the Parkin gene was 1.61, the relative expression of the Atg1 gene was 1.25, the relative expression of the Atg8 gene was 1.02, the relative expression of the FOXO gene was 0.79, and the relative expression of the SIRT1 gene was 4.30. Moreover, compared with the comparison group, the expression levels of the antiaging-related genes in the experimental group were significantly improved, indicating that the yeast powder rich in naturally synthesized nicotinamide mononucleotide can promote the expression levels of the Parkin gene, the Atg1 gene, the Atg8 gene, the FOXO gene and the SIRT1 gene more effectively than the chemically synthesized nicotinamide mononucleotide. In other words, when the subject takes the yeast powder rich in naturally synthesized nicotinamide mononucleotide, the yeast powder can effectively increase the expression levels of the Parkin gene, the Atg1 gene, the Atg8 gene, the FOXO gene and the SIRT1 gene, thereby promoting cell rejuvenation and achieving the antiaging function.

Figure 10:
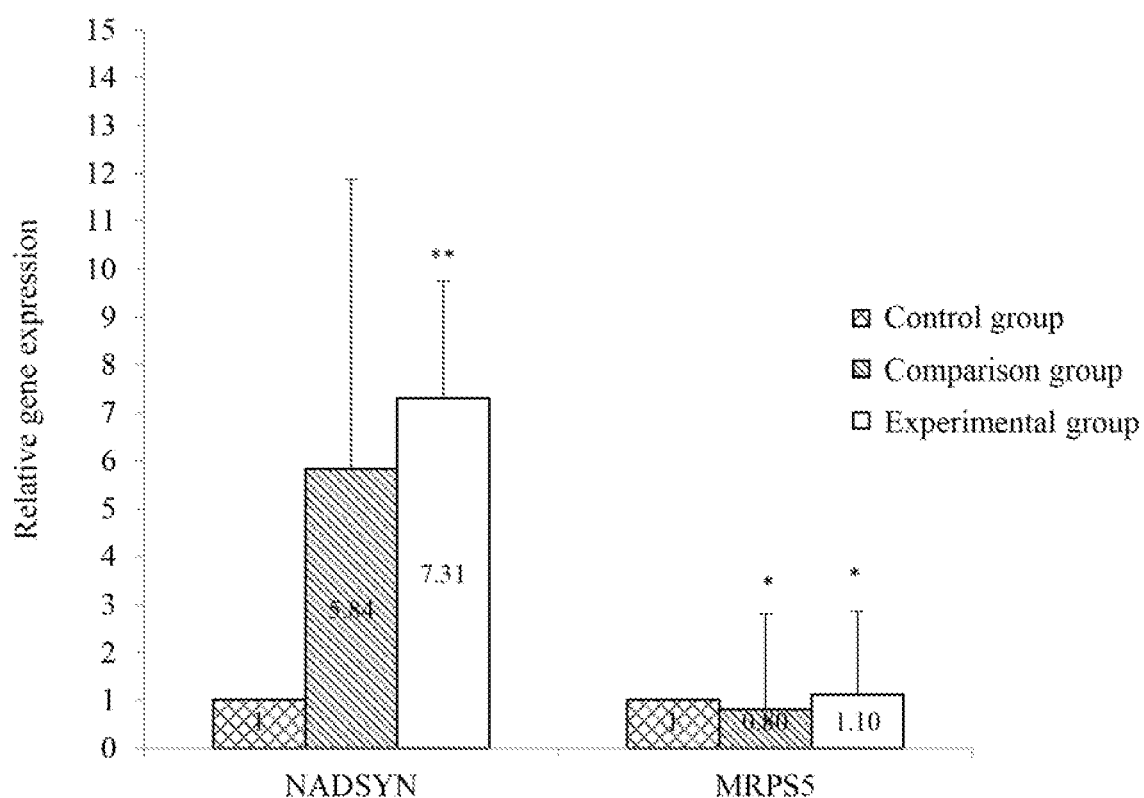
FIG. 10 is a graph showing the experimental result of the relative expression levels of the NADSYN gene and the MRPS5 gene.

Please refer to FIG. 10. The relative expression of each group of NADSYN gene and MRPS5 gene in the control group was regarded as 1.00 (that is, the expression levels of each group of NADSYN gene and MRPS5 gene in the control group was 100%). Compared with the control group, in the experimental group, the relative expression of the NADSYN gene was 7.31 and the relative expression of the MRPS5 gene was 1.10, while in the comparison group, the relative expression of the NADSYN gene was 5.84 and the relative expression of the MRPS5 gene was 0.80. It can thus be seen that the expression levels of the NADSYN gene and MRPS5 gene in the experimental group were significantly higher than the expression levels of the NADSYN gene and the MRPS5 gene in the comparison group, indicating that the yeast powder rich in naturally synthesized nicotinamide mononucleotide can more effectively improve the expression of the NADSYN gene and the MRPS5 gene than the chemically synthesized nicotinamide mononucleotide, thereby enhancing the antiaging and antioxidation capabilities of cells. In other words, when the subject takes the yeast powder rich in naturally synthesized nicotinamide mononucleotide, the yeast powder can effectively increase the expression levels of the NADSYN gene and the MRPS5 gene, thereby achieving the antioxidation and antiaging functions, and promoting cell rejuvenation.

In addition, please refer to FIG. 9 and FIG. 10. The expression levels of the FOXO gene and the MRPS5 gene in the comparison group were lower than those in the control group, indicating that the chemically synthesized nicotinamide mononucleotide would inhibit the expression levels of the FOXO gene and the MRPS5 gene. In other words, not all nicotinamide mononucleotide can promote the expression of antiaging genes.

Example 8: Human Test

To further confirm the effect of the yeast powder rich in nicotinamide mononucleotide (NMN) on a human body, 8 subjects were provided with capsules, each of which contains 100 mg of the yeast powder prepared in Example 1, and each of the subjects took one capsule per day for 8 consecutive weeks. The 8 subjects were healthy men and women between 50 and 75 years old.

The 8 subjects were subjected to blood collection and analysis, complexion test, brain age test and body feeling questionnaire survey before taking the capsules containing the yeast powder (considered as week 0) and 8 weeks after taking the capsules containing the yeast powder (considered as week 8). Blood test items included expression of antiaging-related genes in blood, inflammation indicators (C-reactive protein (CRP) content) in blood, and the low-density lipoprotein cholesterol level and the ratio of low-density lipoprotein cholesterol to high-density lipoprotein cholesterol in blood. The complexion test items included skin wrinkle analysis and skin texture (roughness) analysis. The body feeling questionnaire survey included skin condition, hair loss and fatigue.

It should be noted that the statistically significant difference between the measurement results at week 0 and week 8 was statistically analyzed by a student t-test.

Example 8-1. Human Test: Blood Analysis 6 mL of venous blood of each of the 8 subjects was collected with a purple-head blood collection tube containing an EDTA anticoagulant before taking the yeast powder (week 0) and after taking the yeast powder (week 8), for performing analysis of the expression of the antiaging-related genes in the blood, analysis of inflammation indicators in the blood, and analysis of the low-density lipoprotein cholesterol level and the ratio of low-density lipoprotein cholesterol to high-density lipoprotein cholesterol in the blood.

Example 8-1-1. Analysis of Expression of Antiaging-Related Genes in Blood

Herein, the tested antiaging-related genes are an SIRT1 gene (Gene ID: 23411) and an SOD3 gene (Gene ID: 6649).

Figure 11:
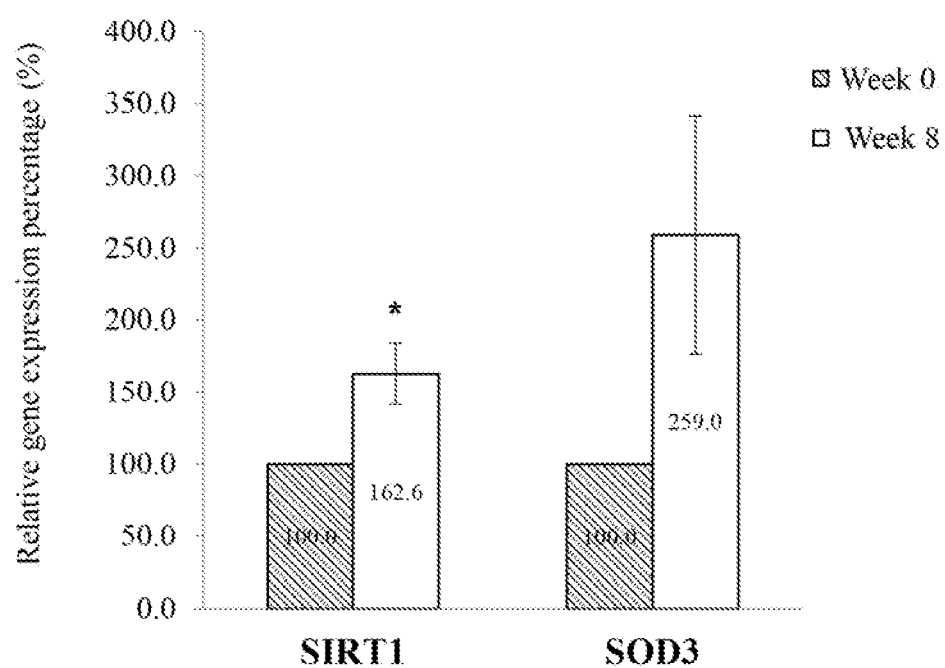
FIG. 11 is a graph showing the experimental result of the relative expression levels of antiaging-related genes at week 0 and week 8.

First, the collected venous blood was centrifuged at 300×g for 15 minutes. 2 mL of buffy coat was taken from the venous blood after centrifugation, and the buffy coat was diluted with 2 mL of phosphate buffer (1×PBS; hereinafter referred to as 1×PBS buffer) to 4 mL. Then the diluted buffy coat was slowly added to a centrifuge tube containing 3 mL of a cell separation solution (Ficoll-Paque Plus cell separation solution), and the diluted buffy coat and the cell separation solution during the addition must be in a layered state and cannot be mixed. Then, the centrifuge tube containing the layered and diluted buffy coat and the cell separation solution was centrifuged at 400×g for 40 minutes, and the supernatant was removed after centrifugation. 2 mL to 3 mL of peripheral blood mononuclear cells (PBMC) in the middle layer of the centrifuge tube after centrifugation was taken. The PBMC was rinsed with 3 times of 1×PBS buffer by volume and then mixed with the 1×PBS buffer to form a PBMC mixture. Then, the PBMC mixture was centrifuged at 300×g for 10 minutes to form a PBMC supernatant and a PBMC precipitate, and the PBMC precipitate was lysed with 600 μL of an RNA lysis buffer to extract RNA. Then, according to the steps in Example 7, after reverse transcription of the extracted RNA into cDNA, two sets of primers (SEQ ID NO: 19 and SEQ ID NO: 20, SEQ ID NO. 25 and SEQ ID NO: 26) in Table 2 were used to perform the quantitative real-time reverse transcription polymerase chain reaction on the cDNA to observe the expression levels of the SIRT1 gene and the SOD3 gene in blood at week 0 and week 8, as shown in FIG. 11.

TABLE 2

| Target gene | Primer name | Sequence No. | Sequence | Primer length |
|---|---|---|---|---|
| SIRT1 | SIRT1-F | SEQ ID NO: 19 | TGCTGGCCTAATAGAGTGGCA | 21 |
|  | SIRT1-R | SEQ ID NO: 20 | CTCAGCGCCATGGAAAATGT | 20 |
| SOD3 | SOD3-F | SEQ ID NO: 25 | AGCTGGAAAGGTGCCCGA | 18 |
|  | SOD3-R | SEQ ID NO: 26 | CTTGGCGTACATGTCTCGGAT | 23 |

In Table 2, F represents a forward primer, and R represents a reverse primer.

It should be specially noted that the gene expression in FIG. 11 was presented in terms of relative expression percentage, an STDEV formula of Excel software was used to calculate standard deviation, and the statistically significant difference among the groups was statistically analyzed by a student t-test. In FIG. 11. "*" represents that the p value is less than 0.05 when compared with the control group.

Please refer to FIG. 11. When the relative gene expression percentages of the SIRT1 gene and the SOD3 gene of the 8 subjects at week 0 were regarded as 100%, at week 8, the relative gene expression percentage of the SIRT1 gene was 162.6%, and the relative gene expression percentage of the SOD3 gene was 259.0%. It can thus be seen that when the subjects took 100 mg of yeast powder daily for 8 weeks, the expression levels of the SIRT7 gene and the SOD3 gene in the subjects' blood were increased, representing that the expression levels of proteins encoded by the SIRT7 gene and the SOD3 gene were increased. Moreover, the SIRT1 gene and the SOD3 gene are the downstream genes of NAD$^+$ and are related to the activity of mitochondria. When the SIRT1 gene and the SOD3 gene in the blood are increased, it reflects the increase in the NAD level in the blood, and the mitochondria can be activated, thereby achieving the function of antiaging. In other words, the increase in the expression levels of the SIRT1 gene and the SOD3 gene in the blood by taking the yeast powder can represent that the yeast powder has the potential to activate mitochondria and resist aging.

Example 8-1-2. Analysis of the Degree of Inflammation in the Blood

Herein, in the experiment, blood was collected from the 8 subjects at week 0 and week 8 to test the changes in the degree of inflammation before and after taking the capsules each of which contains 100 mg of the yeast powder prepared in Example 1. C-reactive protein (CRP) is a special protein produced by the liver, is an acute phase non-specific reactant protein, and is an indicator of tissue damage in the process of acute inflammation. Determined by enzyme-linked immunosorbent assay (ELISA), the higher the level of C-reactive protein in the blood, the more serious the anti-inflammatory reaction in a body. The level of C-reactive protein in the blood of the subjects in this embodiment was determined by Lezen Reference Lab (Taiwan, China).

The level of C-reactive protein was calculated using an STDEV formula of Excel software to calculate the standard deviation, and the statistically significant difference among the groups was statistically analyzed by a student t-test. "*" represents that the p value is less than 0.05 when compared with the control group.

Figure 12:
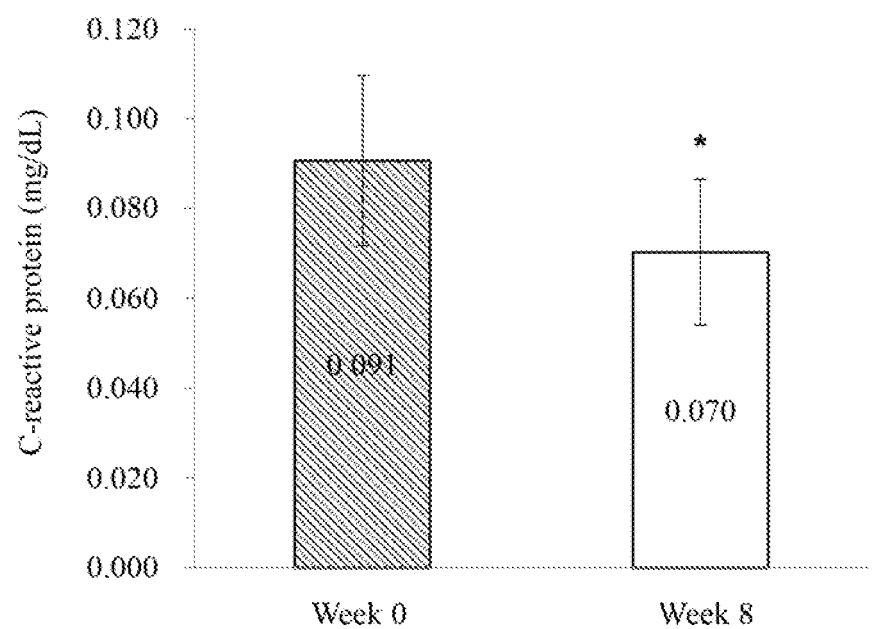
FIG. 12 is a graph showing the experimental result of the C-reactive protein levels at week 0 and week 8.

Please refer to FIG. 12. The average level of C-reactive protein (CRP) in the blood of the 8 subjects at week 0 was 0.091 mg/dL, and the average level of C-reactive protein (CRP) in the blood at week 8 was 0.070 mg/dL, decreased by 0.021 mg/dL (23.1%). That is, the decrease in the level of C-reactive protein (CRP) in the blood by taking the yeast powder represents that the yeast powder has antiinflammatory potential.

Based on this, the subjects daily intake of 100 mg of the yeast powder can significantly reduce the inflammation indicator (C-reactive protein (CRP) content), thereby reducing the uncomfortable symptoms of chronic inflammation.

Example 8-1-3. Analysis of Blood Fat

Low-density lipoprotein cholesterol will invade endothelial cells and cause the cells to be oxidized, increasing the risk of cardiovascular diseases. Therefore, generally, it is desirable to reduce the level of low-density lipoprotein cholesterol. On the contrary, high-density lipoprotein cholesterol can inhibit the occurrence of cardiovascular diseases. Any cholesterol in high-density lipoprotein particles is regarded as a factor that protects the health of the body's cardiovascular system. Therefore, it is generally desirable to increase the level of high-density lipoprotein cholesterol.

Figure 13:
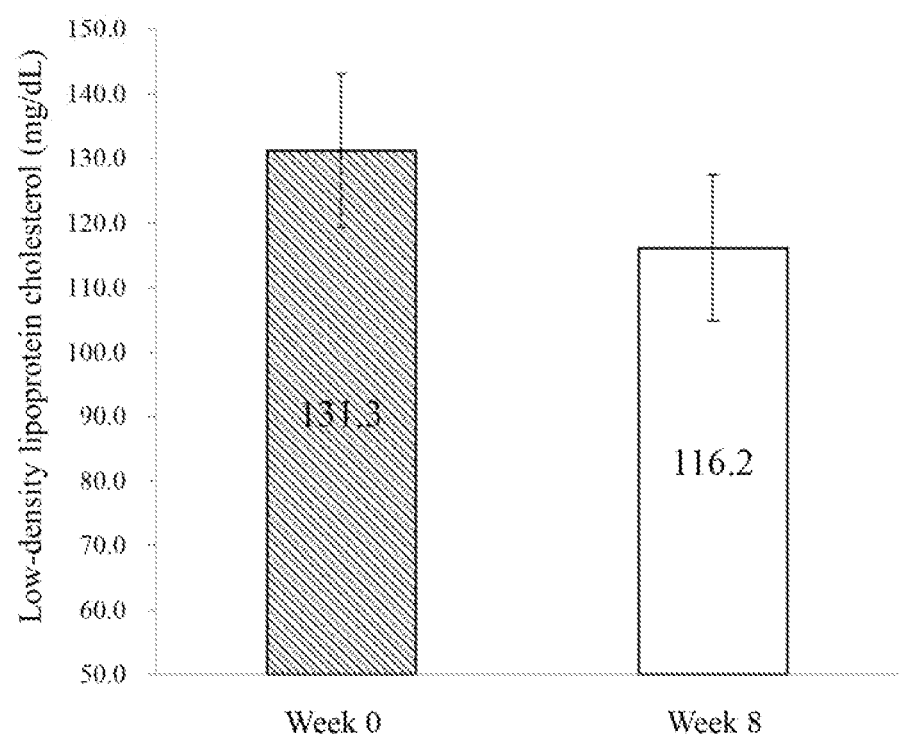
FIG. 13 is a graph showing the experimental result of low-density lipoprotein cholesterol levels at week 0 and week 8.
Figure 14:
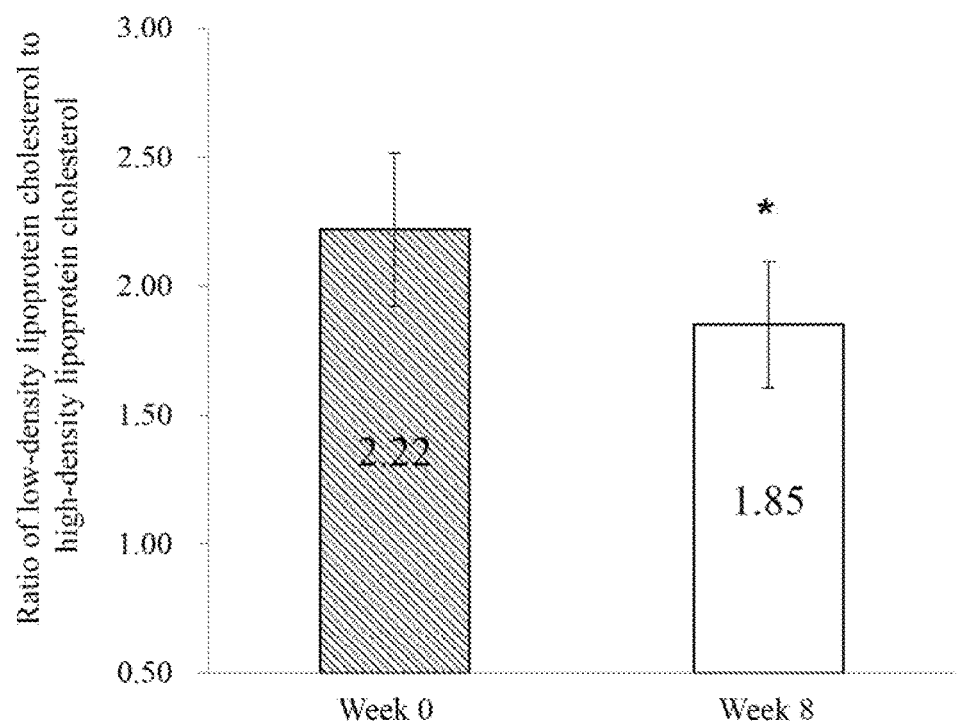
FIG. 14 is a graph showing the experimental result of a ratio of low-density lipoprotein cholesterol to high-density lipoprotein cholesterol at week 0 and week 8.

Herein, blood fat analysis includes test of the low-density lipoprotein cholesterol level and the ratio of low-density lipoprotein cholesterol to high-density lipoprotein cholesterol, determined by Lezen Reference Lab (Taiwan, China). Blood collected at week 0 and week 8 of the 8 subjects were tested for the low-density lipoprotein cholesterol level and the ratio of low-density lipoprotein cholesterol to high-density lipoprotein cholesterol, as shown in FIG. 13 and FIG. 14. In addition, the low-density lipoprotein cholesterol level in FIG. 13 and the ratio of low-density lipoprotein cholesterol to high-density lipoprotein cholesterol in FIG. 14 were calculated using an STDEV formula of Excel software to obtain the standard deviation, and the statistically significant difference among the groups was statistically analyzed by a student t-test. Moreover, "*" represents that the p-value is less than 0.05 when compared with the control group.

Please refer to FIG. 13. The average level of low-density lipoprotein cholesterol in the blood of the 8 subjects at week 0 was 131.3 mg/dL, and the average level of low-density lipoprotein cholesterol in the blood at week 8 was 116.2 mg/dL. It can thus be seen that after the subjects took the yeast powder for 8 weeks, the level of low-density lipoprotein cholesterol in the blood decreased by 15.1 mg/dL, representing that the average level of low-density lipoprotein cholesterol in the blood of the 8 subjects at week 8 decreased by 11.5% compared with the average level of low-density lipoprotein cholesterol in the blood of the 8 subjects at the week 0. In other words, the decrease in the level of low-density lipoprotein cholesterol in the blood by taking the yeast powder prevents arteriosclerosis caused by oxidation of low-density lipoprotein, representing that the yeast powder has the potential for blood fat regulation and cardiovascular health.

Please refer to FIG. 14. The average ratio of low-density lipoprotein cholesterol to high-density lipoprotein cholesterol in the blood of the 8 subjects at week 0 was 2.22, while the average ratio of low-density lipoprotein cholesterol to high-density lipoprotein cholesterol in the blood at week 8 was 1.85, decreased by 0.37 (16.7%). Since the higher the ratio of low-density lipoprotein cholesterol to high-density lipoprotein cholesterol, the higher the risk of coronary atherosclerosis, a decrease in the ratio of low-density lipoprotein cholesterol to high-density lipoprotein cholesterol means a decrease in the risk of coronary atherosclerosis. That is, the ratio of low-density lipoprotein cholesterol to high-density lipoprotein cholesterol in the blood was regulated and decreased by taking the yeast powder, representing that the yeast powder has the potential to regulate blood fat, decrease the risk of coronary atherosclerosis, and maintain cardiovascular health.

Based on this, the subject's daily intake of 100 mg of yeast powder can significantly decrease the inflammation indicator (C-reactive protein (CRP) level) and decrease the risk of coronary atherosclerosis, thereby decreasing the risk of cardiovascular diseases and achieving the function of cardiovascular health.

Example 8-2. Human Test: Complexion Analysis

Herein, the VISA Complexion Analysis System (Canfield scientific, USA) was used for skin condition analysis. The skin wrinkles of the same subject's facial skin were photographed using a high-resolution camera lens before and after the subject takes the yeast powder. By illuminating with standard white light and detecting the change of skin shadow, the texture position can be detected and a value can be obtained to represent the smoothness of the skin. The skin texture was detected on the facial skin of the same subject before and after the subject takes the yeast powder. The principle is to take high-resolution skin images with visible light, and the roughness of the skin was analyzed using built-in software according to the concave and convex of the skin. The higher the measurement value, the rougher the skin.

Figure 15:
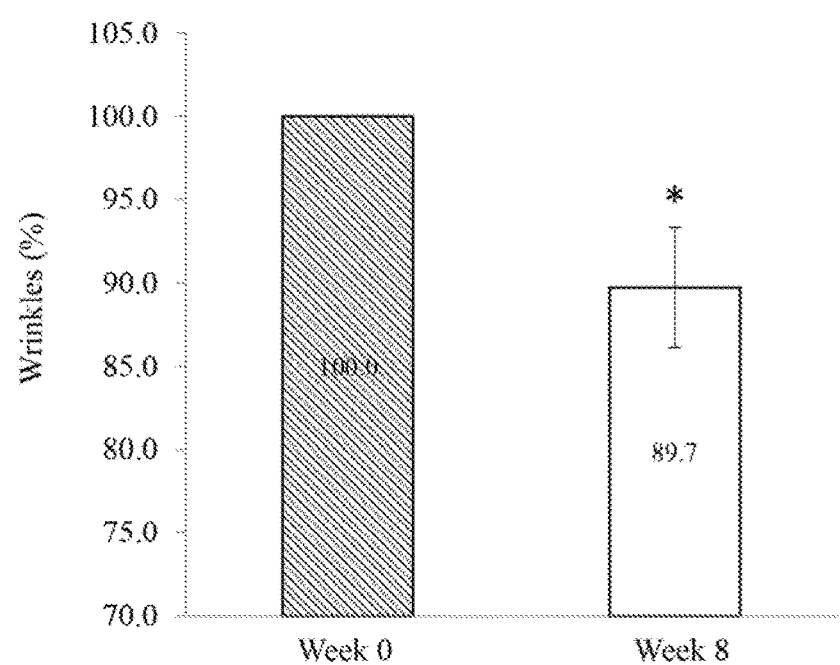
FIG. 15 is a graph showing the experimental result of the percentage of wrinkles at week 0 and week 8.

Please refer to FIG. 15. The average skin wrinkle percentage detected by the VISIA Complexion Analysis System of the 8 subjects before taking the yeast powder (week 0) was regarded as 100%. After the subjects continuously taking the yeast powder for 8 weeks, their average skin wrinkle percentage dropped to 89.7%. In other words, compared with that before taking the yeast powder (week 0), after 8 weeks of continuous intake of capsules each of which contains 100 mg of yeast powder, the skin wrinkle percentage of the subjects was decreased by 10.3%. It can thus be seen that long-term intake of the yeast powder rich in nicotinamide mononucleotide (NMN) can reduce the skin wrinkles of the subject and improve the skin condition of the subjects. That is, the yeast powder has an effect of smoothening fine wrinkles.

In addition, one of the subjects had many and dense wrinkles WK-0 photographed by the VISIA Complexion Analysis System before taking the yeast powder (week 0), while after taking the yeast powder (week 8), the number of wrinkles WK-8 photographed decreased and became sparser. Based on this, long-term intake of the yeast powder rich in nicotinamide mononucleotide can reduce the number of wrinkles on the subject's face.

Figure 16:
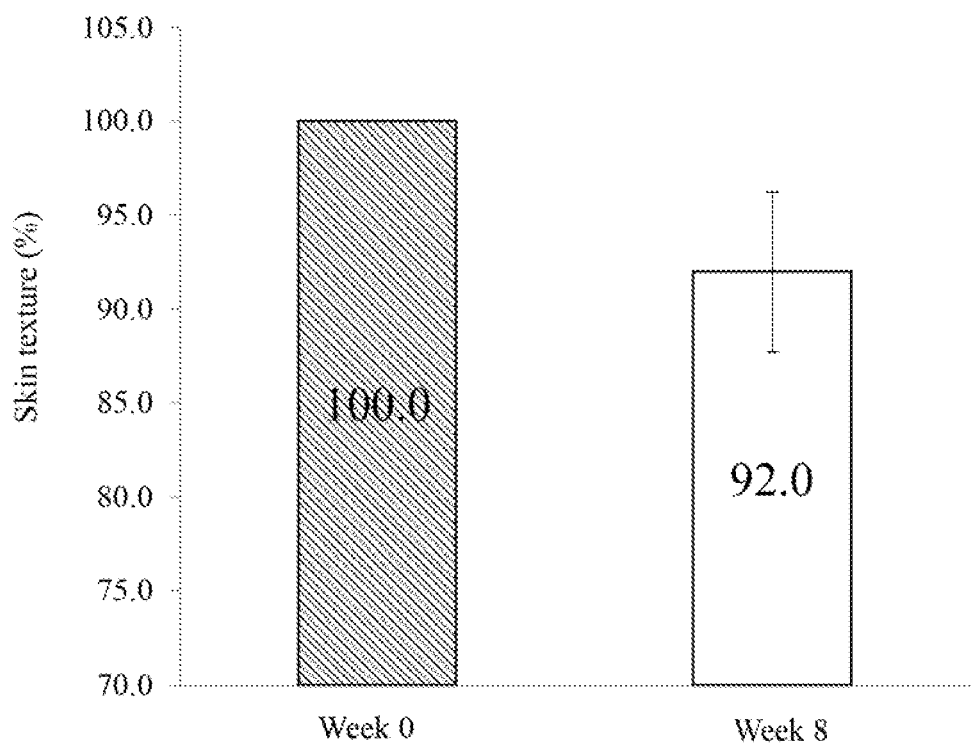
FIG. 16 is a graph showing the experimental result of the percentage of skin texture at week 0 and week 8.

Please refer to FIG. 16. The average skin texture percentage detected by the VISIA Complexion Analysis System of the 8 subjects before taking the yeast powder (week 0) was regarded as 100%. After the subjects continuously taking the yeast powder for 8 weeks, their average skin texture percentage dropped to 92.0%. In other words, compared with that before taking the yeast powder (week 0), after 8 weeks of continuous intake of capsules each of which contains 100 mg of yeast powder, the skin texture percentage of the subjects was decreased by 8.0%. It can thus be seen that long-term intake of the yeast powder rich in nicotinamide mononucleotide can reduce the skin texture of the subject and reduce the skin roughness of the subject, so as to achieve the effect of improving the skin condition of the subject. That is, the yeast powder has the effect of making the skin fine.

In addition, one of the subjects had many and dense bumps T-0 photographed by the VISIA Complexion Analysis System before taking the yeast powder (week 0), while after taking the yeast powder (week 8), the number of bumps T-8 photographed was decreased and became sparser. Based on this, long-term intake of the yeast powder rich in nicotinamide mononucleotide can reduce the bumps on the subject's face, thereby reducing the roughness of the skin and making the subject's skin fine.

Example 8-3. Human Test: Brain Age Analysis

Herein, before taking the yeast powder (week 0) and after taking the yeast powder (week 8), the "Test Your Brain Age" software was used to test the brain age of the 8 subjects. Specifically, the "Test Your Brain Age" software calculates the subject's brain age based on the subject's overall correct answer rate and response speed. The test items include selecting the number displayed on the screen from small to big before the number displayed on the screen disappears.

"Test Your Brain Age" software website is: https://apps.apple.com/tw/app/test-your-brain-age/id969455998.

Figure 17:
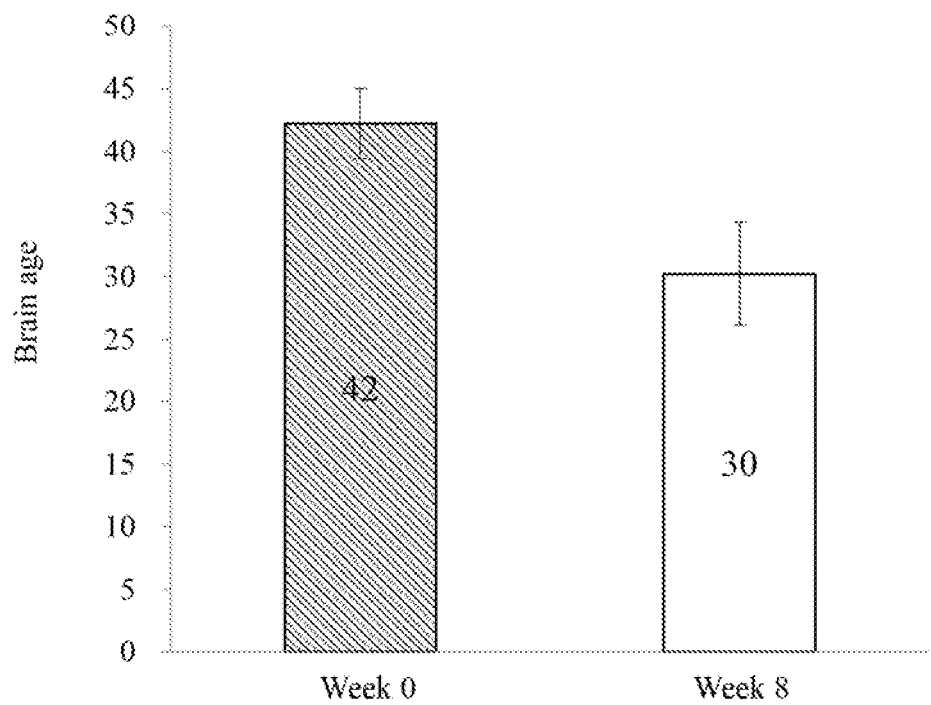
FIG. 17 is a graph showing the experimental result of the brain age at week 0 and week 8.

Please refer to FIG. 17. The average brain age of the 8 subjects before taking the yeast powder (week 0) was 42 years. After the subjects continuously taking the yeast powder for 8 weeks, their average brain age dropped to 30 years. In other words, compared to that before taking the yeast powder (week 0), continuous intake of capsules each of which contains 100 mg of yeast powder for 8 weeks can reduce the average brain age of the subjects by 12 years, representing that after the subjects took the yeast powder for 8 weeks, their brain thoughts were clearer, and the response speed of answering questions was also improved.

It can thus be seen that long-term intake of the yeast powder rich in nicotinamide mononucleotide (NMN) can make the mind clearer, and reduce the subject's brain age, thereby achieving an antiaging effect, that is, the yeast powder has the effects of clearing mind and resisting aging.

Example 8-4. Human Test: Body Feeling Questionnaire Survey

Herein, the subjects filled out a body feeling questionnaire at week 0 and week 8, and the body feeling questionnaire included a comprehensive assessment of physical state. The subjects would assess the severity of their physical conditions (for example, poor overall skin condition, hair loss condition, hair scantiness condition and body fatigue), as shown in Table 3.

TABLE 3

Comprehensive assessment of physical state

| Symptom | Severity | | | | |
|---|---|---|---|---|---|
| | None (1) | Mild (2) | Overt (3) | Severe (4) | Very severe (5) |
| 1. Poor overall skin condition | | | | | |
| 2. Hair loss condition | | | | | |
| 3. Hair scantiness condition | | | | | |
| 4. Body fatigue | | | | | |

In Table 3, "None" represents 1 point, "Mild" represents 2 points, "Overt" represents 3 points, "Severe" represents 4 points, and "Very severe" represents 5 points. After adding up the scores, the severity of each test item is calculated.

Figure 18:
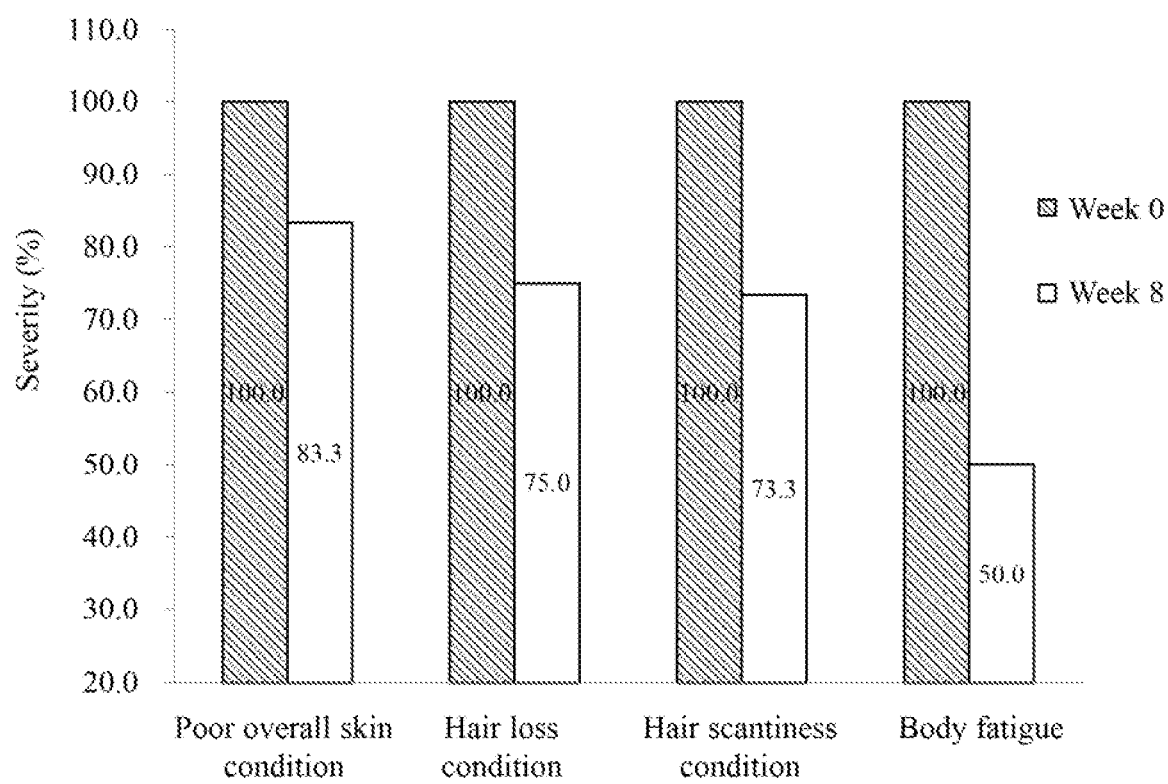
FIG. 18 is a graph showing the experimental result of comprehensive assessment of the physical state at week 0 and week 8.

Please refer to FIG. 18. The average severity of the "poor overall skin condition" of the 8 subjects before the subjects take the yeast powder (week 0) was regarded as 100%. After 8 weeks of continuous intake of the yeast powder (that is, week 8), the average severity of "poor overall skin condition" dropped to 83.3%. In other words, compared with that before taking the yeast powder (week 0), after 8 weeks of continuous intake of capsules containing the yeast powder, the 8 subjects' perception of "poor skin condition" was decreased by 16.7%, representing that the yeast powder rich in nicotinamide mononucleotide could improve the skin condition of the subjects.

The average severity of the "hair loss condition" of the 8 subjects before taking the yeast powder (week 0) was regarded as 100%. After 8 weeks of continuous intake of the yeast powder (that is, week 8), the average severity of the "hair loss condition" dropped to 75.0%. In other words, compared with that before taking the yeast powder (week 0), after 8 weeks of continuous intake of capsules containing the yeast powder, the 8 subjects' perception of "hair loss condition" was decreased by 25.0%, representing that the yeast powder rich in nicotinamide mononucleotide could reduce the hair loss condition of the subjects.

The average severity of the "hair scantiness condition" of the 8 subjects before taking the yeast powder (week 0) was regarded as 100%. After 8 weeks of continuous intake of the yeast powder (that is, week 8), the average severity of the "hair scantiness condition" dropped to 73.3%. In other words, compared with that before taking the yeast powder (week 0), after 8 weeks of continuous intake of capsules containing the yeast powder, the 8 subjects' perception of "hair scantiness condition" was decreased by 26.7%, representing that the yeast powder rich in nicotinamide mononucleotide could reduce the hair scantiness condition of the subjects, and improve the hair thickness of the subjects.

The average severity of "body fatigue" of the 8 subjects before taking the yeast powder (week 0) was regarded as 100%. After 8 weeks of continuous intake of the yeast powder (that is, week 8), the average severity of "body fatigue" dropped to 50.0%1a. In other words, compared with that before taking the yeast powder (week 0), after 8 weeks of continuous intake of capsules containing the yeast powder, the 8 subjects' perception of "body fatigue" was decreased by 50.0%, representing that the yeast powder rich in nicotinamide mononucleotide could reduce the body fatigue of the subjects, raise the subjects' spirit and make the subjects more vigorous.

It can thus be seen that long-term intake of the yeast powder rich in nicotinamide mononucleotide can improve the overall skin condition, hair loss condition and fatigue of the subjects.

Example 9. Sequencing Analysis of Peptides in Yeast Powder Rich in Nicotinamide Mononucleotide After the yeast powder rich in nicotinamide mononucleotide prepared in Example 1 was appropriately diluted and centrifuged (13000 rpm, 2 min), 200 μl of supernatant was pipetted, and desalted and concentrated using CIS-ZipTip (Milipore). After being re-dissolved, ½ by volume of a sample was taken and subjected to LC-MS/MS analysis under the following conditions. A Mascot analysis program was used to perform database search and analysis on an MS/MS map to obtain analysis results, and then obtain the protein sequence and identification information of peptides contained in the yeast powder.

Reaction Conditions:
Mass spectrometer: LTQ XL (Thermo Scientific)
LC system: Agilent 1200 Series
Buffer solution A: ddH$_2$O/0.1% formic acid
Buffer solution B: 100% ACN/0.1% formic acid
Analytical column: C18 reverse phase column
The gradients are as follows: B % is 5% at minute 0.00, 13% is 5% at minute 10.02, B % is 5% at minute 10.05, B % is 40% at minute 45.00, B % is 85% at minute 50.00, B % is 85% at minute 60.00, B % is 5% at minute 63.00, B % is 5% at minute 75.02, B % is 5% at minute 75.05, and B % is 5% at minute 90.00.

Analysis result: The protein identification information of the peptide contained in the yeast powder rich in nicotinamide mononucleotide was ubiquinone biosynthesis protein, and the protein sequence of the analyzed peptide was: MVAKAHSKK (SEQ ID NO: 27). It can thus be seen that the yeast powder rich in nicotinamide mononucleotide contains peptide fragments of ubiquinone biosynthesis protein.

In summary, according to the preparation method of the yeast powder rich in nicotinamide mononucleotide of any embodiment of the present invention, the yeast powder containing at least 5000 ppm of nicotinamide mononucleotide can be prepared, solving the problem that traditional nicotinamide mononucleotide can only be chemically synthesized and harmful by-products are generated in the production process, and at the same time solving the technical bottleneck that traditional nicotinamide mononucleotide is inedible and can only be externally used. The components of the fermentation medium used in any embodiment of the preparation method include nicotinamide, tryptophan and niacin. Also, the components of the fermentation medium used in any embodiment of the preparation method further include the *Solanum* plant extract, the *Aronia* plant extract, the *Musa* plant extract, or any combination thereof. The yeast powder prepared by any embodiment of the preparation method can be used to prepare a composition for improving skin condition, hair health, antiinflammation, cardiovascular health, antioxidation, antiaging, and/or relieving body fatigue. In other words, the composition has one or more of the following functions: resisting cell oxidative stress, improving cell mitochondrial activity, regulating antiaging-related genes (that is, inhibiting the PARP2 gene, and improving the CCT genes, the Parkin gene, the Atg1 gene, the Atg8 gene, the FOXO gene, the SIRT1 gene, the NADSYN gene, the MRPS5 gene and the SOD3 gene), reducing skin wrinkles and skin texture, rejuvenating the brain (decreasing the brain age), reducing the hair loss condition, reducing the hair scantiness degree, and reduce body fatigue. In addition, the yeast powder of any embodiment further includes ubiquinone biosynthesis protein.

Although the technical content of the present invention has been disclosed with reference to the preferred embodiments above, the embodiments are not intended to limit the present invention. Various variations and modifications made by any person skilled in the art without departing from the spirit of the present invention shall fall within the scope of the present invention. Therefore, the protection scope of the present invention shall be subject to those defined in the attached claims.

Certainly, the present invention may further have a plurality of other embodiments. A person skilled in the art may make various corresponding changes and variations according to the present invention without departing from the spirit and essence of the present invention. However, such corresponding changes and variations shall fall within the protection scope of the claims appended to the present invention.

What is claimed is:

1. A preparation method of yeast powder rich in nicotinamide mononucleotide, comprising:
preparing a first medium, a second medium and a third medium, wherein components of the first medium, the second medium and the third medium comprise nicotinamide, tryptophan, and niacin;
inoculating the first medium with yeast for fermentation to obtain a first fermentation broth;
inoculating the second medium with the first fermentation broth for fermentation to obtain a second fermentation broth;
inoculating the third medium with the second fermentation broth for fermentation to obtain a third fermentation broth; and
centrifuging the third fermentation broth to obtain a fermented product, and drying the fermented product to obtain the yeast powder, wherein a content of the nicotinamide mononucleotide in the yeast powder is at least 5000 ppm.

2. The preparation method according to claim 1, wherein the first medium is inoculated with the yeast at an inoculum amount of 5 vol %; the second medium is inoculated with the first fermentation broth at an inoculum amount of 6 vol %; and the third medium is inoculated with the second fermentation broth at an inoculum amount of 10 vol %.

3. The preparation method according to claim 1, wherein a concentration of the nicotinamide is 0.01 wt % to 0.3 wt %, a concentration of the tryptophan is 0.1 wt % to 0.5 wt %, and a concentration of the niacin is 0.001 wt % to 0.06 wt %.

4. The preparation method according to claim 1, wherein a volume ratio of the first medium to the second medium to the third medium is 3:50:500.

5. The preparation method according to claim 1, wherein the yeast powder further comprises ubiquinone biosynthesis protein (COQ).

6. The preparation method according to claim 1, wherein the components of the first medium, the second medium and the third medium further comprise a *Solanum* plant extract, an *Aronia* plant extract, a *Musa* plant extract, or any combination thereof.

* * * * *